US006187748B1

(12) United States Patent
Maddon et al.

(10) Patent No.: US 6,187,748 B1
(45) Date of Patent: Feb. 13, 2001

(54) USES OF CD4-GAMMA2 AND CD4-IGG2 CHIMERAS

(75) Inventors: Paul J. Maddon, New York, NY (US); Gary A. Beaudry, Upper Montclair, NJ (US)

(73) Assignee: Progenics Pharmaceuticals, Inc., Tarrytown, NY (US)

( * ) Notice: Under 35 U.S.C. 154(b), the term of this patent shall be extended for 0 days.

(21) Appl. No.: 08/485,372

(22) Filed: Jun. 7, 1995

Related U.S. Application Data

(63) Continuation-in-part of application No. 07/960,440, filed as application No. PCT/US92/01143 on Feb. 10, 1992, now abandoned, which is a continuation-in-part of application No. 07/653,684, filed on Feb. 8, 1991, now abandoned.

(51) Int. Cl.[7] ............................. A61K 38/00; C12N 15/62

(52) U.S. Cl. ........................... 514/12; 435/69.7; 536/23.4
(58) Field of Search ........................... 514/12; 424/185.1; 435/69.7; 536/23.4

(56) References Cited

U.S. PATENT DOCUMENTS

| | | | |
|---|---|---|---|
| 4,664,911 | 5/1987 | Uhr et al. | 424/182.1 |
| 5,116,964 | 5/1992 | Capon et al. | 536/23.5 |
| 5,565,335 | 10/1996 | Capon et al. | 435/69.7 |

FOREIGN PATENT DOCUMENTS

| | | |
|---|---|---|
| 0314317 | 5/1989 | (EP) . |
| 0394827 | 10/1990 | (EP) . |
| WO8801304 | 2/1989 | (WO) . |
| WO8901940 | 3/1989 | (WO) . |
| WO8902922 | 4/1989 | (WO) . |
| WO8903222 | 4/1989 | (WO) . |
| WO8906690 | 7/1989 | (WO) . |
| WO9001035 | 2/1990 | (WO) . |
| WO9100360 | 1/1991 | (WO) . |
| WO9213559 | 8/1992 | (WO) . |

OTHER PUBLICATIONS

Byrn, R.A. et al. (1990) Biological properties of CD4 Immunoadhesin, Nature, vol. 344: 667–670.

Capon, D.J. et al. (1989) Designing CD4 Immunoadhesins for AIDS Therapy, Nature, vol. 337: 525–531.

Chamow, S.M. et al. (1990) Enzymatic Cleavage of a CD4 Immunoadhesin generates Crystallizable Biologically Active FD–Like Fragments, Biochemistry, vol. 29, No. 42:9885–9891.

Chowdhury, et al. (1991) Evaluation of anti–human Immunodeficiency Virus Affect of Recombinant CD4–Immunoglobin In–Vitro: A good candidate for AIDS treatment, Microbiol. Immunol., vol. 180, No.4: 183–192.

Maddon, et al. (1985) The Isolation and Nucleotide Sequence of a cDNA Encoding the T Cell Surface Protein T4: A new member of the Immunoglobin Gene Family, Cell, vol. 42: 93–104.

Morrison, S.L. et al. (1984) Chimeric Human Antibody Molecules: Mouse Antigen–binding domains with Human Constant Region Domains, Proc. Nat. Acad. Sci., vol. 81, 6851–6855.

Murray, J.L. et al. (1985) Radioimaging in Malignant Melanoma with [111]In–labeled Monoclonal Antibody 96.5 Cancer Research, vol. 45: 2376–2381.

Pastan, I. et al. (1989) Pseudomonas Exotoxin: Chimeric Toxins, J. Biological Chemistry, vol. 264, No. 26: 15157–15160.

Pastan, I. et al. (1991) Recombinant Toxins for Cancer Treatment, Science, vol. 254:1173–1177.

Till, M.A. et al. (1988) HIV–Infected Cells are Killed by rCD4–Ricin A Chain, Science, vol. 242:1166–1168.

Traunecker, A. et al. (1989) Highly efficient Neutralization of HIV with Recombinant CD4–Immunoglobin Molecules, Nature, vol.339: 68–70.

Gilboa et al. Trends in Genetics 10, 139–144, 1994.

Goodman et al, in Basic and Clinical Immunology, Eighth Edition. Eds. Stites et al. Norwalk, CT: Appleton & Lange, 1994.

Fahey et al. Clin. Exp. Immunol. 88, 1–5, 1992.

Auffray et al. Tibtech 9, 124–131, 1991.

*Primary Examiner*—John Ulm
(74) *Attorney, Agent, or Firm*—John P. White; Cooper & Dunham LLP

(57) ABSTRACT

This invention provides the CD4-IgG2 chimeric heterotetramer, wherein the heavy chains of the chimeric heterotetramer is encoded by the expression vector designated CD4-IgG2HC-pRcCMV (ATCC No. 75193). This invention also provides the CD4-IgG2 chimeric heterotetramer, wherein the light chains of the chimeric heterotetramer is encoded by the expression vector designated CD4-kLC-pRcCMV (ATCC No. 75194). This invention also provides the CD4-IgG2 chimeric heterotetramer, wherein the heavy chains of the chimeric heterotetramer is encoded by the expression vector designated CD4-IgG2HC-pRcCMV (ATCC No. 75193) and the light chains of the chimeric heterotetramer is encoded by the expression vector designated CD4-kLC-pRcCMV (ATCC No. 75194). Finally, this invention provides a method of inhibiting HIV infection of a CD4+ cell, a method of preventing a subject from being infected with HIV, and a method of treating a subject infected with HIV so as to block the spread of HIV infection, using the above CD-4-IgG2 chimeric heterotetramers.

3 Claims, 29 Drawing Sheets

FIGURE 2A
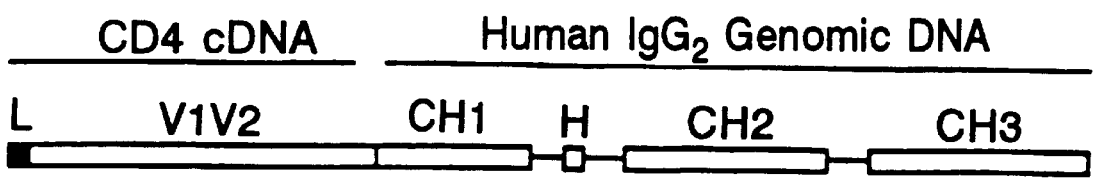
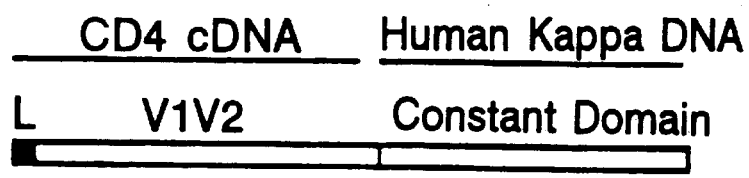
FIGURE 2B
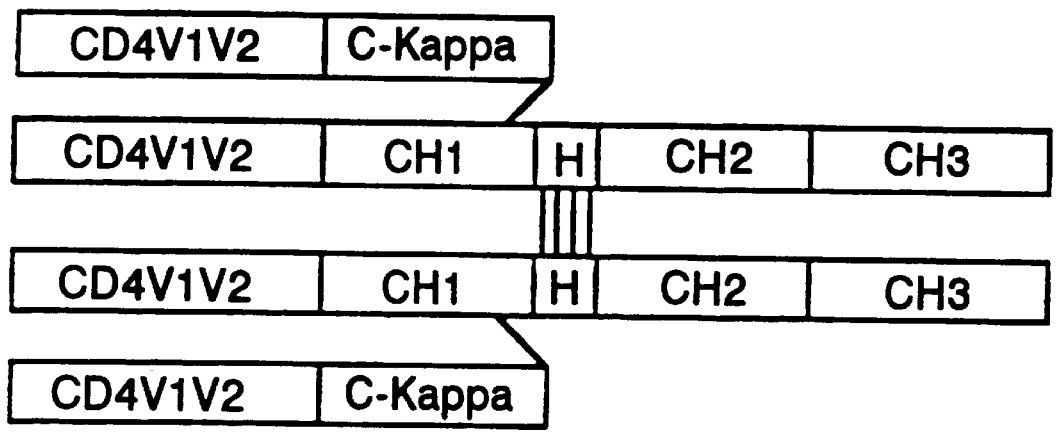

FIGURE 3A

```
CAAGCCCAGAGCCCTGCCATTTCTGTGGGCTCAGGTCCCTACTGCTCAGCCCCTT       55
                                    →CD4
                              -20
                         M   N   R   G   V   P   F   R   H
CCTCCCTCGGCAAGGCCACAATG  AAC CGG GGA GTC CCT TTT AGG CAC       102
            -10
 L   L   V   L   Q   L   A   L   L   P   A   A   T
TTG CTT GTG CTG CAA CTG GCG CTC CTC CCA GCA GCC ACT            144
                                     +10
 -1  +1
 Q   G   K   K   V   V   L   G   K   K   G   D   T   V
CAG GGA AAG AAA GTG GTG CTG GGC AAA AAA GGG GAT ACA GTG        186
                         +20
 E   L   T   C   T   A   S   Q   K   K   S   I   Q   F
GAA CTG ACC TGT ACA GCT TCC CAG AAG AAG AGC ATA CAA TTC        228
         +30                                         +40
 H   W   K   N   S   N   Q   I   K   I   L   G   N   Q
CAC TGG AAA AAC TCC AAC CAG ATA AAG ATT CTG GGA AAT CAG        270
                                 +50
 G   S   F   L   T   K   G   P   S   K   L   N   D   R
GGC TCC TTC TTA ACT AAA GGT CCA TCC AAG CTG AAT GAT CGC        312
```

FIGURE 3B

```
  G   S   F   L   T   K   G   P   S   K   L   N   D   R
GGC TCC TTC TTA ACT AAA GGT CCA TCC AAG CTG AAT GAT CGC   312
                    +60

A   D   S   R   R   S   L   W   D   Q   G   N   F   P
GCT GAC TCA AGA AGA AGC CTT TGG GAC CAA GGA AAC TTC CCC   354
                                            +80

L   I   I   K   N   L   K   I   E   D   S   D   T   Y
CTG ATC ATC AAG AAT CTT AAG ATA GAA GAC TCA GAT ACT TAC   396
        +70

I   C   E   V   E   D   Q   K   E   E   V   Q   L   L
ATC TGT GAA GTG GAG GAC CAG AAG GAG GAG GTG CAA TTG CTA   438
                            +90                  +110

V   F   G   L   T   A   N   S   D   T   H   L   Q
GTG TTC GGA TTG ACT GCC AAC TCT GAC ACC CAC CTG CTT CAG   480
            +100

G   Q   S   L   T   L   E   S   P   P   G   S
GGG CAG AGC CTG ACC TTG GAG AGC CCC CCT GGT AGT           522
                            +120

S   P   S   V   Q   C   R   S   P   R   G   K   N   I
AGC CCC TCA GTG CAA TGT AGG AGT CCA AGG GGT AAA AAC ATA   564
                +130
```

FIGURE 3C

```
      +140                              +150
   Q   G   G   K   T   L   S   V   S   Q   L   E   L   Q
  CAG GGG GGG AAG ACC CTC TCC GTG TCT CAG CTG GAG CTC CAG    606

+160
   D   S   G   T   W   T   C   T   V   L   Q   N   Q   K
  GAT AGT GGC ACC TGG ACA TGC ACT GTC TTG CAG AAC CAG AAG    648

┌→Hinge
                   +170                           +180  E
   K   V   E   F   K   I   D   I   V   V   L   A   F   E
  AAG GTG GAG TTC AAA ATA GAC ATC GTG GTG CTA GCT TTC GAG    690

+190
   R   K   C   C   V   E   C   P   P   C   P
  CGC AAA TGT TGT GTC GAG TGC CCA CCG TGC CCA GGTAAGCCAGCC   705

CAGGCCTCGCCCCTCCAGCTCAAGGCGGGACAGGTGCCCTAGAGTAGCCTGCATCC   760
                                                    ┌→CH2
                                                    A
  AGGGACAGGCCCCAGCTGGGTGCTGACACGTCCACCTCCATCTCTTCCTCAGCA     814

+200
   P   P   V   A   G   P   S   V   F   L   F   P   P   K
  CCA CCT GTG GCA GGA CCG TCA GTC TTC CTC TTC CCC CCA AAA    856
```

FIGURE 3D

```
     P   K   D   T   L   M   I   S   R   T   P   E   V   T
    +210
                     L
    CCC AAG GAC ACC CTC ATG ATC TCC CGG ACC CCT GAG GTC ACG    898

+220
     C   V   V   V   D   V   S   H   E   D   P   E   V   Q
                                         +230
    TGC GTG GTG GTG GAC GTG AGC CAC GAA GAC CCC GAG GTC CAG    940

F   N   W   Y   V   D   G   V   E   V   H   N   A   K
                        +240
    TTC AAC TGG TAC GTG GAC GGC GTG GAG GTG CAT AAT GCC AAG    982

T   K   P   R   E   E   Q   F   N   S   T   F   R   V
         +250                                        +260
    ACA AAG CCA CGG GAG GAG CAG TTC AAC AGC ACG TTC CGT GTG   1024

V   S   V   L   T   V   V   H   Q   D   W   L   N   G
                                     +270
    GTC AGC GTC CTC ACC GTT GTG CAC CAG GAC TGG CTG AAC GGC   1066

K   E   Y   K   C   K   V   S   N   K   G   L   P   A
                 +280
    AAG GAG TAC AAG TGC AAG GTC TCC AAC AAA GGC CTC CCA GCC   1108

P   I   E   K   T   I   S   K   T   K
    +290
    CCC ATC GAG AAA ACC ATC TCC AAA ACC AAAGGTGGGACCCGCGGGG   1154
```

FIGURE 3E

```
TATGAGGGCCACATGGACAGAGAGGCCGGCTCGGCCCACCCTCTGCCCTGGGAGTGA          1209
                              └→CH3
                               +300
                           G   Q   P   R   E   E   P   Q
CCGCTGTGCCAACCTCTGTCCCTACAGGG CAG CCC CGA GAA CCA CAG              1256

+320
 V   Y   T   L   P   P   S   R   E   E   M   T   K   N
GTG TAC ACC CTG CCC CCA TCC CGG GAG GAG ATG ACC AAG AAC            1298

+330
 Q   V   S   L   T   C   L   V   K   G   F   Y   P   S
CAG GTC AGC CTG ACC TGC CTG GTC AAA GGC TTC TAC CCC AGC            1340

+340                             +360
 D   I   A   V   E   W   E   S   N   G   Q   P   E   N
GAC ATC GCC GTG GAG TGG GAG AGC AAT GGG CAG CCG GAG AAC            1382

+350                                         D   G   S
 N   Y   K   T   T   P   P   M   L   D   S   D   G   S
AAC TAC AAG ACC ACA CCT CCC ATG CTG GAC TCC GAC GGC TCC            1424

+370
 F   F   L   Y   S   K   L   T   V   D   K   S   R   W
TTC TTC CTC TAC AGC AAG CTC ACC GTG GAC AAG AGC AGG TGG            1466
```

FIGURE 3F

```
        +380                                           +400
 Q   Q   G   N   V   F   S   C   S   V   M   H   E   A
CAG CAG GGG AAC GTC TTC TCA TGC TCC GTG ATG CAT GAG GCT   1508

+410
 L   H   N   H   Y   T   Q   K   S   L   S   L   S   P
CTG CAC AAC CAC TAC ACG CAG AAG AGC CTC TCC CTG TCT CCG   1550

G   K  stop
GGT AAA TGAGTGCCACGGCCGGCAAGCCCCCGCTCCCCAGGCTCTCGGGGTCG   1603

CGTGAGGATGCTTGGCACCCCGTGTACATACTTCCCAGCCACCCAGCATGG       1658

AAATAAAGCACCCAGCGCTGCCCTGGGCCCTGCGAGACTGTGATGGTTCTTTCC    1713

GTGGGTCAGGCCGAGTCTGAGGCCTGAGTGGCATGAGGGAGGCAGAGTGGGTC...  1766
```

FIGURE 4A

```
CAAGCCCAGAGCCCTGCCATTTCTGTGGGCTCAGGTCCCTACTGCTCAGCCCCTT                            55
        └─►CD4
                         -20
         M   N   R   G   V   P   F   R   H
CCTCCCCTCGGCAAGGCCACAATG AAC CGG GGA GTC CCT TTT AGG CAC                            102

-10
 L   L   L   V   L   Q   L   A   L   L   P   A   A   T
TTG CTT CTG GTG CTG CAA CTG GCG CTC CTC CCA GCA GCC ACT                             144

-1  +1                                          +10
 Q   G   K   K   V   V   L   G   K   K   G   D   T   V
CAG GGA AAG AAG GTG GTG CTG GGC AAA AAG GGG GAT ACA GTG                             186

+20
 E   L   T   C   T   A   S   Q   K   K   S   I   Q   F
GAA CTG ACC TGT ACA GCT TCC CAG AAG AAG AGC ATA CAA TTC                             228

+30                                 +40
 H   W   K   N   S   N   Q   I   K   I   L   G   N   Q
CAC TGG AAA AAC TCC AAC CAG ATA AAG ATT CTG GGA AAT CAG                             270

+50
 G   S   F   L   T   K   G   P   S   K   L   N   D   R
GGC TCC TTC TTA ACT AAA GGT CCA TCC AAG CTG AAT GAT CGC                             312
```

FIGURE 4B

```
  A   D   S   R   R   S   L   W   D   Q   G   N   F   P
GCT GAC TCA AGA AGA AGC CTT TGG GAC CAA GGA AAC TTC CCC    354
                        +60                    +80
  L   I   I   K   N   L   K   I   E   D   S   D   T   Y
CTG ATC ATC AAG AAT CTT AAG ATA GAA GAC TCA GAT ACT TAC    396
    +70                        +90
  I   C   E   V   E   D   Q   K   E   E   V   Q   L   L
ATC TGT GAA GTG GAG GAC CAG AAG GAG GAG GTG CAA TTG CTA    438
                                               +110
  V   F   G   L   T   A   N   S   D   T   H   L   L   Q
GTG TTC GGA TTG ACT GCC AAC TCT GAC ACC CAC CTG CTT CAG    480
        +100
  G   Q   S   L   T   L   T   L   E   S   P   P   G   S
GGG CAG AGC CTG ACC CTG ACC TTG GAG AGC CCC CCT GGT AGT    522
                                   +120
  S   P   S   V   Q   C   R   S   P   R   G   K   N   I
AGC CCC TCA GTG CAA TGT AGG AGT CCA AGG GGT AAA AAC ATA    564
                +130
```

FIGURE 4C

```
     +140
      Q   G   G   K   T   L   S   V   S   Q   L   E   L   Q
     CAG GGG GGG AAG ACC CTC TCC GTG TCT CAG CTG GAG CTC CAG    606
                                             +150

D   S   G   T   W   T   C   T   V   L   Q   N   Q   K
     GAT AGT GGC ACC TGG ACA TGC ACT GTC TTG CAG AAC CAG AAG    648
                      +160                            →CH1
                                                      +180
      K   V   E   F   K   I   D   I   V   V   L   A   F   A
     AAG GTG GAG TTC AAA ATA GAC ATC GTG GTG CTA GCT TTC GCC    690
              +170

S   T   K   G   P   S   V   F   P   L   A   P   C   S
     TCC ACC AAG GGC CCA TCG GTC TTC CCC CTG GCG CCC TGC TCC    732
                          +190

R   S   T   S   E   S   T   A   A   L   G   C   L   V
     AGG AGC ACC TCC GAG AGC ACA GCC GCC CTG GGC TGC CTG GTC    774
                          +200

K   D   Y   F   P   E   P   V   T   V   S   W   N   S
     AAG GAC TAC TTC CCC GAA CCG GTG ACG GTG TCG TGG AAC TCA    816
          +210                                +220

G   A   L   T   S   G   V   H   T   F   P   A   V   L
     GGC GCT CTG ACC AGC GGC GTG CAC ACC TTC CCA GCT GTC CTA    858
                              +230
```

FIGURE 4D

```
      +240                            +250
  Q   S   S   G   L   Y   S   L   S   V   V   T   V
CAG TCC TCA GGA CTC TAC TCC CTC AGC AGC GTG GTG ACC GTG    900

+260
  P   S   N   F   G   T   Q   T   Y   T   C   N   V
CCC TCC AGC AAC TTC GGC ACC CAG ACC TAC ACC TGC AAC GTA    942

+270
  D   H   K   P   S   N   T   K   V   D   K   T   V
GAT CAC AAG CCC AGC AAC ACC AAG GTG GAC AAG ACA GTTGGTG    985

AGAGGCCAGCTCAGGGAGGAGGGTGTCTGCTGGAAGCCAGGCTCAGCCCTCCTG    1040

CCTGGACGCACCCCGGCTGTGCAGCCCCAGCGCCCTCTGCCCGGCCACTCTGT    1095

CTGTCTCCTCACCCGGAGGCCTCTGCCCGCCCCACTCATGCTCAGGGAGAGGGTC   1150

TTCTGGCTTTTTCCACCAGGCTCCAGGCACAGGCTCAGGCAGGCAGGCCCCAT    1205

GGCCCTTCACACACAGGGGCAGGTGCTTGGCTCAGACCTGCCAAAAGCCATATCC   1260
```

FIGURE 4E

```
GGGAGGACCCTGCCCCTGACCCTAAGCCGACCCCAAGGCCAAACTGTCCACTCCC                    1315

TCAGCTCGGACACCTTCTCTCCTCCCAGATCCGAGTAACTCCCAATCTTCTCTCT                    1370
      →Hinge
        +280
GCAGAG CGC AAA TGT TGT GTC GAG TGC CCA CCG TGC CCA GGTAAG                  1415
  E    R   K   C   C   V   E   C   P   P   C   P

CCAGCCCAGGCCTCGCCCCTCCAGCTCAAGGCGGGACCAGGTGCCCTAGAGTAGCCT                  1470

GCATCCAGGAGGACAGGCCCCAGCTGGGTGCTGACACGTCCACCTCCATCTCTCTCCT                 1525
      →CH2                                         +300
       +290
 A    P   P   V   A   G   P   S   V   F   L   F   P   P
CAGCA CCA CCT GTG GCA GGA CCG TCA GTC TTC CTC TTC CCC CCA                  1569

+310
 K    P   K   D   T   L   M   I   S   R   T   P   E   V
AAA  CCC AAG GAC ACC CTC ATG ATC TCC CGG ACC CCT GAG GTC                   1611

+320                             +330
 T    C   V   V   V   D   V   S   H   E   D   P   E   V
ACG  TGC GTG GTG GTG GAC GTG AGC CAC GAA GAC CCC GAG GTC                   1653
```

FIGURE 4F

```
      Q   F   N   W   Y   V   D   G   V   E   V   H   N   A
     CAG TTC AAC TGG TAC GTG GAC GGC GTG GAG GTG CAT AAT GCC        1695
                              +340

K   T   K   P   R   E   E   Q   F   N   S   T   F   R
     AAG ACA AAG CCA CGG GAG GAG CAG TTC AAC AGC ACG TTC CGT        1737
                      +350

+360
      V   V   S   V   L   T   V   V   H   Q   D   W   L   N
     GTG GTC AGC GTC CTC ACC GTT GTG CAC CAG GAC TGG CTG AAC        1779
                                              +370

G   K   E   Y   K   C   K   V   S   N   K   G   L   P
     GGC AAG GAG TAC AAG TGC AAG GTC TCC AAC AAA GGC CTC CCA        1821
                                  +380

+390
      A   P   I   E   K   T   I   S   K   T   K
     GCC CCC ATC GAG AAA ACC ATC TCC AAA ACC AAAGGTGGGACCCGC        1866

GGGGTATGAGGGCCACATGGACAGAGGCCGGCTCGGCCCACCCTCTGCCCTGGGA        1921
                                              →CH3
                                                +400
      G   Q   P   R   E   P   Q
     GTGACCGCTGTGCCAACCTCTGTCCCTACAGGG CAG CCC CGA GAA CCA CAG      1972
```

FIGURE 4G

```
      V   Y   T   L   P   P   S   R   E   E   M   T   K   N
     GTG TAC ACC CTG CCC CCA TCC CGG GAG GAG ATG ACC AAG AAC    2014
           +410
+420
      Q   V   S   L   T   C   L   V   K   G   F   Y   P   S
     CAG GTC AGC CTG ACC TGC CTG GTC AAA GGC TTC TAC CCC AGC    2056
                               +430
      D   I   A   V   E   W   E   S   N   G   Q   P   E   N
     GAC ATC GCC GTG GAG TGG GAG AGC AAT GGG CAG CCG GAG AAC    2098
                       +440
           +450                              +460
      N   Y   K   T   T   P   P   M   L   D   S   D   G   S
     AAC TAC AAG ACC ACA CCT CCC ATG CTG GAC TCC GAC GGC TCC    2140
      F   F   L   Y   S   K   L   T   V   D   K   S   R   W
     TTC TTC CTC TAC AGC AAG CTC ACC GTG GAC AAG AGC AGG TGG    2182
                                       +470
           +480
      Q   Q   G   N   V   F   S   C   S   V   M   H   E   A
     CAG CAG GGG AAC GTC TTC TCA TGC TCC GTG ATG CAT GAG GCT    2224
+490                                              +500
      L   H   N   H   Y   T   Q   K   S   L   S   L   S   P
     CTG CAC AAC CAC TAC ACG CAG AAG AGC CTC TCC CTG TCT CCG    2266
```

FIGURE 4H

```
  G   K  stop
GGT AAA TGAGTGCCACGGGCCGGCAAGCCCCCGTCCCCAGGCTCTCGGGTCG        2319

CGTGAGGATGCTTGGCACGTACCCCGTGTACATACTTCCCAGGCACCCAGCATGG       2374

AAATAAAGCACCCAGCGCTGCCCTGGGCCCCTGCGAGACTGTGATGGTTCTTTCC       2429

GTGGGTCAGGCCCGAGTCTGAGGCCCTGAGTGGCATGAGGAGGCAGAGTGGGTC...     2482
```

FIGURE 5A

```
CAAGCCCAGAGCCCTGCCATTTCTGTGGGCTCAGTCCCTACTGCTCAGCCCTT                                    55
                            └→CD4
                                         -20
              M   N   R   G   V   P   F   R   H
CCTCCCCTCGGCAAGGCCACAATG AAC CGG GGA GTC CCT TTT AGG CAC                                 102
         -10
  L   L   L   V   L   Q   L   A   L   L   P   A   A   T
CTG CTT CTG GTG CTG CAA CTG GCG CTC CTC CCA GCA GCC ACT                                  144
                                                    +10
 -1  +1
  G   K   K   V   V   L   G   K   K   G   D   T   V
CAG AAG AAA GTG GTG CTG GGC AAA AAA GGG GAT ACA GTG                                      186
                        +20
  E   L   T   C   T   A   S   Q   K   K   S   I   Q   F
GAA CTG ACC TGT ACA GCT TCC CAG AAG AAG AGC ATA CAA TTC                                  228
             +30                                      +40
  H   W   K   N   S   N   Q   I   K   I   L   G   N   Q
CAC TGG AAA AAC TCC AAC CAG ATA AAG ATT CTG GGA AAT CAG                                  270
                                  +50
  G   S   F   L   T   K   G   P   S   K   L   N   D   R
GGC TCC TTC TTA ACT AAA GGT CCA TCC AAG CTG AAT GAT CGC                                  312
```

FIGURE 5B

```
 A   D   S   R   R       L   W   D   Q   G   N   F   P
                        +60
                         S
GCT GAC TCA AGA AGA AGC CTT TGG GAC CAA GGA AAC TTC CCC    354

L   I   I   K   N   L   K   I   E   D   S   D   T   Y
+70                                     +80
 I
CTG ATC ATC AAG AAT CTT AAG ATA GAA GAC TCA GAT ACT TAC    396

I   C   E   V   E   D   Q   K   E   E   V   Q   L   L
                            +90
ATC TGT GAA GTG GAG GAC CAG AAG GAG GAG GTG CAA TTG CTA    438

V   F   G   L   T   A   N   S   D   T   H   L   L   Q
    +100                                        +110
GTG TTC GGA TTG ACT GCC AAC TCT GAC ACC CAC CTG CTT CAG    480

G   Q   S   L   T   L   T   L   E   S   P   P   G   S
                                    +120
GGG CAG AGC CTG ACC CTG ACC TTG GAG AGC CCC CCT GGT AGT    522

S   P   S   V   Q   C   R   S   P   R   G   K   N   I
            +130
AGC CCC TCA GTG CAA TGT AGG AGT CCA AGG GGT AAA AAC ATA    564
```

FIGURE 5C

```
      +140
      Q    G    G    K    T    L    S    V    S    Q    L    E    L    Q
      CAG  GGG  GGG  AAG  ACC  CTC  TCC  GTG  TCT  CAG  CTG  GAG  CTC  CAG    606
                              +160                          +150
      D    S    G    T    W    T    C    T    V    L    Q    N    Q    K
      GAT  AGT  GGC  ACC  TGG  ACA  TGC  ACT  GTC  TTG  CAG  AAC  CAG  AAG    648
                +170                                              →Ckappa
                                                                    +180
      K    V    E    K    I    D    I    V    V    L    A    F    T    T
      AAG  GTG  GAG  TTC  AAA  ATA  GAC  ATC  GTG  GTG  CTA  GCT  TTC  ACT    690
                                              +190
      V    A    A    P    S    V    F    I    F    P    P    S    D    E
      GTG  GCT  GCA  CCA  TCT  GTC  TTC  ATC  TTC  CCG  CCA  TCT  GAT  GAG    732
                                    +200
      Q    L    K    S    G    T    A    S    V    V    C    L    L    N
      CAG  TTG  AAA  TCT  GGA  ACT  GCC  TCT  GTT  GTG  TGC  CTG  CTG  AAT    774
      +210                                                    +220
      N    F    Y    P    R    E    A    K    V    Q    W    K    V    D
      AAC  TTC  TAT  CCC  AGA  GAG  GCC  AAA  GTA  CAG  TGG  AAG  GTG  GAT    716
                                              +230
      N    A    L    Q    S    G    N    S    Q    E    S    V    T    E
      AAC  GCC  CTC  CAA  TCG  GGT  AAC  TCC  CAG  GAG  AGT  GTC  ACA  GAG    758
```

FIGURE 5D

```
     +240                                    +250
 Q    D    S    K    D    S    T    Y    S    L    S    S    T    L
CAG  GAC  AGC  AAG  GAC  AGC  ACC  TAC  AGC  CTC  AGC  AGC  ACC  CTG    900

+260
 T    L    S    K    A    D    Y    E    K    H    K    V    Y    A
ACG  CTG  AGC  AAA  GCA  GAC  TAC  GAG  AAA  CAC  AAA  GTC  TAC  GCC    942

+270
 C    E    V    T    H    Q    G    L    S    S    P    V    T    K
TGC  GAA  GTC  ACC  CAT  CAG  GGC  CTG  AGC  TCG  CCC  GTC  ACA  AAG    984

+280
 S    F    N    R    G    E    C   stop
AGC  TTC  AAC  AGG  GGA  GAG  TGT  TAG  AGGGAGAAGTGCCCCACCTGCTC         1032

CTCAGTTCCAGCCTGACCCCTTGGCCTCTGACCCTTTTCCACAGG                          1088

GGACCTACCCCCTATTGCGGTCCTCCAAGCTCATCTTTCACCTCACCCCCCCTCC                1144

TCCTT
```

USES OF CD4-GAMMA2 AND CD4-IGG2 CHIMERAS

This application is a continuation-in-part of U.S. Ser. No. 07/960,440, filed Dec. 8, 1992, now abandoned, which is a national stage application of PCT International Application No. PCT/US92/01143, filed Feb. 10, 1992, claiming priority of and a continuation-in-part of U.S. Ser. No. 07/653,684, filed Feb. 8, 1991, now abandoned.

BACKGROUND OF THE INVENTION

Throughout this application, various publications are referenced by Arabic numerals within parentheses. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein.

The life cycle of animal viruses is characterized by a series of events that are required for the productive infection of the host cell. The initial step in the replicative cycle is the attachment of the virus to the cell surface which is mediated by the specific interaction of the viral attachment protein (VAP) to receptors on the surface of the target cell. The pattern of expression of these receptors is largely responsible for the host range and tropic properties of viruses. The interaction of the VAP with cellular receptors therefore plays a critical role in infection and pathogenesis of viral diseases and represents an important area to target the development of anti-viral therapeutics.

Cellular receptors may be comprised of all the components of membranes, including proteins, carbohydrates, and lipids. Identification of the molecules mediating the attachment of viruses to the target cell surface has been made in a few instances. The most extensively characterized viral receptor protein is CD4 (T4) (1). CD4 is a nonpolymorphic cell surface glycoprotein that is expressed primarily on the surface of helper T lymphocytes and cells of the monocyte/macrophage lineage. CD4 associates with major histocompatibility complex (MHC) class II molecules on the surface of antigen-presenting cells to mediate efficient cellular immune response interactions. In man, CD4 is also the target of interaction with the human immunodeficiency virus (HIV).

HIV infects primarily helper T lymphocytes and monocytes/macrophages, cells that express surface CD4, leading to a gradual loss of immune function which results in the development of the human acquired immune deficiency syndrome (AIDS). The initial phase of the HIV replicative cycle involves the high affinity interaction between the HIV exterior envelope glycoprotein gp120 and surface CD4 (Kd approximately $4 \times 10^{-9}$ M) 2). Several lines of evidence demonstrate the requirement of this interaction for viral infectivity. In vitro, the introduction of a functional cDNA encoding CD4 into human cells which do not express CD4 is sufficient to render otherwise resistant cells susceptible to HIV infection (3). In vivo, viral infection appears to be restricted to cells expressing CD4. Following the binding of HIV gp120 to cell surface CD4, viral and target cell membranes fuse, resulting in the introduction of the viral capsid into the target cell cytoplasm.

Characterization of the interaction between HIV gp120 and CD4 has been facilitated by the isolation of cDNA clones encoding both molecules (4, 5). CD4 is a nonpolymorphic, lineage-restricted cell surface glycoprotein that is a member of the immunoglobulin gene superfamily. High-level expression of both full-length CD4 and truncated, soluble versions of CD4 (sCD4) have been described in stable expression systems. The availability of large quantities of purified sCD4 has permitted a detailed understanding of the structure of this complex glycoprotein. Mature CD4 has a relative molecular mass (Mr) of 55 kilodaltons and consists of an amino-terminal 372 amino acid extracellular domain containing four tandem immunoglobulin-like regions denoted V1–V4, followed by a 23 amino acid transmembrane domain and a 38 amino acid cytoplasmic segment. The amino-terminal immunoglobulin-like domain V1 bears 32% homology with kappa light chain variable domains. Three of the four immunoglobulin-like domains contain a disulphide bond (V1, V2 and V4), and both N-linked glycosylation sites in the carboxy-terminal portion of the molecule are utilized (4, 6).

Experiments using truncated sCD proteins demonstrate that the determinants of high-affinity binding to HIV gp120 lie within the amino-terminal immunoglobulin-like domain V1 (7–9). Mutational analysis of V1 has defined a discrete gp120 binding site (residues 38–52 of the mature CD4 protein) that comprises a region structurally homologous to the second complementarity-determining region (CDR2) of immunoglobulins (9). The production of large quantities of V1V2 has permitted a structural analysis of the two amino-terminal immunoglobulin-like domains. The structure determined at 2.3 angstrom resolution reveals that the molecule has two tightly associated domains containing the immunoglobulin-fold connected by a continuous beta strand. The putative binding sites for monoclonal antibodies, class II MHC molecules and HIV gp120 (as determined by mutational analysis) map on the molecular surface (10, 11).

A soluble version of the entire extracellular segment of CD4 (V1–V4, termed sCD4) has been described and appears to be a potential therapeutic approach to the treatment of HIV infection 12). In vitro experiments demonstrate that: 1) SCD4 acts as a "molecular decoy" by binding to HIV gp120 and inhibiting viral attachment to and subsequent infection of human cells; 2) sCD4 "strips" the viral envelope glycoprotein gp120 from the viral surface; and 3) sCD4 blocks the intercellular spread of virus from HIV-infected cells to uninfected cells by inhibiting virus-mediated cell fusion (1, 13).

In addition to in vitro results, experiments with sCD4 in simian immunodeficiency virus (SIV)-infected rhesus monkeys have been described. These studies demonstrated that administration of 2 milligrams (intramuscular) of sCD4 for 28 days to SIV-infected rhesus monkeys led to a decreased ability to isolate virus from peripheral blood lymphocytes and bone marrow. In addition, the growth of granulocyte-macrophage and erythrocyte progenitor colonies in the bone marrow returned to normal levels. These data suggest that administration of sCD4 to SIV-infected rhesus monkeys leads to a diminution of the viral reservoir.

Phase I human clinical trials demonstrated that there is no significant toxicity or immunogenicity associated with administration of sCD4 at does as high as 30 mg/day. Pharmocokinetic studies revealed the serum half-life of sCD4 to be 45 minutes following intravenous administration, 9.4 hours after intramuscular dosing, and 10.3 hours after the drug was given subcutaneously (14, 15). Preliminary antiviral studies were inconclusive with respect to CD4 cell count and levels of HIV antigen. Because the maximum tolerated dose was not reached, the antiviral effect of sCD4 may have been underestimated, especially in light of recent data concerning differences in sCD4 concentrations required to inhibit laboratory strains of HIV-1 compared to primary viral isolates (16).

Although these in vitro, primate, and human clinical studies with sCD4 have produced encouraging results, they have also defined several limitations. First, the measured serum half-life of sCD4 is relatively short. Second, sCD4 is monovalent with respect to gp120 binding in contrast with cell surface CD4 and viral surface gp120 which are multivalent. Third, sCD4 is not cytotoxic for HIV-infected cells. Fourth, sCD4 may not cross the placenta to a significant degree. Therefore, chimeric CD4 molecules have been described which take advantage of the immunoglobulin-like nature of CD4 and several beneficial properties of immunoglobulins themselves (i.e. CD4-immunoglobulin fusions).

Immunoglobulins, or antibodies, are the antigen-binding molecules produced by B lymphocytes which comprise the humoral immune response. The basic unit of an immunoglobulin molecule consists of two identical heavy chains and two identical light chains. The amino-terminus of each chain contains a region of variable amino acid sequence (variable region). The variable regions of the heavy and light chains interact to form two antigen binding sites. The carboxy-terminus of each chain contains a region of constant amino acid sequence (constant region). The light chain contains a single constant domain, whereas the heavy chain constant domain is subdivided into four separate domains (CH1, hinge, CH2, and CH3). The heavy chains of immunoglobulin molecules are of several types, including mu (M), delta (D), gamma (G), alpha (A) and epsilon (E). The light chains of immunoglobulin molecules are of two types, either kappa or lambda. Within the individual types of heavy and light chains exist subtypes which may differ in effector function. An assembled immunoglobulin molecule derives its name from the type of heavy chain that it possesses.

The development of monoclonal antibodies has circumvented the inherent heterogeneity of antibodies obtained from serum of animals or humans. However, most monoclonal antibodies are derived from cells or mouse origin and therefore are immunogenic when administered to humans. More recent developments combining the techniques of molecular genetics with monoclonal antibody technology has lead to the production of "humanized" chimeric antibodies in vitro. In these chimeric antibodies, the variable domains of human immunoglobulin heavy and light chains are replaced with specific heavy and light chain variable domains from a murine monoclonal antibody (17–19). The result of this genetic manipulation is a molecule with specificity for a particular antigen and the characteristics of human immunoglobulins.

Sequence and structural analyses of CD4 indicate that the four extracellular domains are immunoglobulin-like. Since the Fc portion of immunoglobulins controls the rate of catabolism of the molecules (serum half-life ranging from 14 to 21 days) and provides various effector functions, several reports describe the replacement of variable and constant domains of immunoglobulins with the immunoglobulin-like domains of CD4 (21–24).

CD4-IgG1 heavy chain fusion proteins resulting in chimeric gamma1 heavy chain dimers have been described (21). These molecules contain the gamma1 heavy chain CH1 domain in addition to the hinge, CH2 and CH3 domains. However, heavy chain assembly and secretion from mammalian cells is less efficient if the CH1 domain is expressed in the absence of light chains (25). Subsequently, a CD4-IgG1 heavy chain fusion protein lacking the CH1 domain and the first five amino acids of the hinge region was described which was secreted to high levels (22). These fusion proteins retain various effector functions of immunoglobulin molecules, such as Fc receptor binding, antibody-dependent cell-mediated cytotoxicity (ADCC) toward HIV-1-infected cells, and placental transfer via an Fc receptor-dependent mechanism (22). CD4-IgM heavy chain fusion proteins have also been described (26). In addition, CD4-IgG1 fusion proteins have been described wherein the V1V2 domains of CD4 are fused to the CH1, hinge, CH2 and CH3 domains of a gamma1 heavy chain, and wherein the V1V2 domains of CD4 are fused to the constant domain of a kappa light chain (29).

Fusion proteins linking CD4 to toxins have also been constructed and tested for their ability to kill HIV-infected cells. In one study, sCD4 was coupled to the deglycosylated A chain of ricin which inactivities ribosomes, therefore inhibiting protein synthesis and killing the cell (27). This fusion protein was reported to specifically lyse cells infected with five different isolates of HIV, but was nontoxic to uninfected cells. In another study, the V1V2 domains of CD4 were coupled to domains II and III of Pseudomonas exotoxin A (28). This fusion protein was reported to specifically bind and inhibit protein synthesis in cells expressing the HIV envelope glycoprotein gp120 (25).

It is well established that human monocytes and macrophages (M/M) express surface CD4, can be infected by HIV, and serve as a reservoir of infection and a vehicle for viral dissemination (29). Furthermore human M/M also contain Fc receptors, which are responsible for binding to specific IgG molecules via their Fc portion (see Table 1). The high affinity Fc receptor (FcRI) binds monomeric IgG and complexed IgG (antigen plus antibody). The rank order of affinity of FcRI for IgG isotypes is IgG1=IgG3>IgG4, and does not interact with IgG2. The low affinity Fc receptor (FcRII) binds monomeric IgG with lower affinity than IgG in complexed form. The rank order of affinity is that IgG1 and IgG3 binding is greater than that of Ig2 or IgG4 (30).

| FcReceptor | Molecular Weight | Affinity | Expression | Affinity for isotypes |
| --- | --- | --- | --- | --- |
| FcRI | 72,000 | High | Monocytes | IgG1, IgG3> IgG4, does not bind IgG2 |
| FcRII | 40,000 | Low | Monocytes, platelets, neutrophils | IgG1, IgG3> IgG2, IgG4 |
| FcRIII | 50–70,000 | Low | Neutrophils NK, K, monocytes | IgG1, IgG3 |

(Table abbreviated from Gergely J. and Sarmay G. (1990) FASEB J. 4:3275

Because of the recent demonstration that HIV+ patients' sera contain low titer antibodies which recognize the HIV envelope glycoprotein, it has been observed that infection of M/M is enhanced by low titer anti-HIV antibodies, presumably by cross bridging HIV and the Fc receptor (31). Enhance infection of macrophages by Dengue virus, Yellow fever virus, and Sindbis virus, is well documented in vitro as well as in Rhesus monkeys (32). Such enhancements has been demonstrated to occur in the presence of subneutralizing antibodies to these viruses, which serves to opsonize the viruses and bind them to the FcRs (or complement receptors) on the surface of the cell. In the case of HIV, this crossbridging serves to concentrate HIV onto the surface of the M/M, whereupon the virus is then able to utilize CD4 for entry into the cell, since sCD4 is able to inhibit the enhancement seen with low titer antibodies (31).

Recently, Byrn et al. (22) have produced a CD4-IgG chimera of the IgG1 isotype, to increase the plasma half-life of sCD4 as well as to confer effector functions to the chimeric molecule. Therefore this molecule has the potential to bind to Fc receptors located on the surface of the M/M, and potentially cause an increase in the infection of these cell types. Because enhanced infection of these cell types is a serious consideration in developing novel therapeutics, our objective for designing a CD4-IgG molecule was to use the IgG2 type, which has a greatly diminished ability to bind M/M Fc receptors (30). Furthermore, human IgG2 antibodies appear to lack significant allotypic variation, whereas human IgG1 antibodies contain allotypic variations (33). Therefore, to avoid potential immunogenic responses to recombinant molecules containing immunoglobulin domains, we have chosen a molecule which is the least polymorphic and has a decreased ability to concentrate HIV onto the surface of the macrophage.

Second, similar observations of enhanced infection of unborn babies may also be demonstrated for CD4-IgG1 immunoadhesions administered to pregnant mothers. For example, it is well documented that the placental syncytiotrophoblast plasma membrane contains Fc receptors (30). Because materno-fetal transport of immunoglobulin is primarily restricted to the IgG class, it is believed that passive immunity can be achieved by specific transport across the placenta via a specific Fc receptor transcytotic mechanism. Further, it appears that the Fc receptors on the placental syncytiotrophoblast membrane are selective in that immunoglobulins of the IgG1 type have approximately 10–20 fold higher binding affinity for the receptor. In fact, of all the IgG subtypes, IgG1 and 3 have the highest affinity for the receptor, followed by IgG4, and finally IgG2 (30). These results are consistent with those obtained from the cloning of the FcR from a human placenta, which indicate that the receptor is very similar to the FcRII type found on M/M. Although one might argue that transplacental transport of immunoglobulin may be beneficial to the fetus in utero, it could also be argued that specific maternal immunoglobulin raised to a specific pathogen (such as HIV), might facilitate transport across the placenta via an Fc dependent mechanism, to increase infection of the fetus, similar to the mechanism which has evolved to transport IgA across epithelia, via the poly Ig receptor (34). Thus specific CD4-IgG1 fusion proteins, which have been demonstrated to cross the placenta and concentrate in the fetal blood (22), may be detrimental to the fetus, by providing HIV with a novel mechanism to cross the placental barrier.

We have now discovered that a specific CD4-gamma2 chimeric heavy chain homodimer provides advantages relative to those CD4-IgG1 heavy chain homodimers which have been described more than one year ago. Specifically, we have constructed a CD4-gamma2 chimeric heavy chain homodimer which contains the V1V2 domains of CD4 and which is efficiently assembled intracellularly and efficiently secreted from mammalian cells as a homodimer, enabling high recovery and purification from the medium of cells expressing this chimeric heavy chain homodimer. To construct this homodimer, we have used the entire hinge, CH2, and CH3 domains from a human gamma2 heavy chain, which results in a chimeric molecule containing the constant domains of a human IgG2 molecule responsible for dimerization and efficient secretion. This is in contrast to the heavy chain dimers described by Capon and Gregory (20) which include the CH1 domain in the CD4-IgG1 heavy chain dimer, resulting in poor secretion and recovery from cell culture medium of the recombinant molecule. We have also included the entire hinge domain of gamma2 heavy chain in the CD4-gamma2 chimeric heavy chain homodimer of this invention to provide efficient dimerization, since the cysteine residues contained in this domain are responsible for forming the disulphide links to the second chain of the homodimer, positioning the two chains in the correct spatial alignment and facilitating formation of the antigen combining site.

Furthermore, by including the entire hinge domain, we have maintained the segmental flexibility of the heavy chain dimers, thus enabling modulation of biological function such as complement activation and Fc receptor binding (29).

Since IgG2 immunoglobulins have a greatly diminished ability to bind to Fc receptors on monocytes, macrophages, and placental membranes, construction of a CD4-gamma2 chimeric heavy chain homodimer and a CD4-IgG2 chimeric heterotetramer results in chimeric proteins with many advantages that CD4-gamma1 chimeric heavy chain homodimers or CD4-IgG1 chimeric heterotetramers may not possess (20, 23, 24, 26). Furthermore, human IgG2 is significantly less polymorphic than other IgG types and therefore is less likely to be immunogenic when administered to humans. This is in contrast to human IgG1 which contain many allotypes and has a higher probability of being immunogenic when administered to humans.

In addition to the CD4-gamma2 chimeric heavy chain homodimers, we have also constructed CD4-IgG2 heavy chains, which contain the V1V2 domains of CD4 fused to the CH1, hinge, CH2 and CH3 domains of human gamma2 heavy chain. These molecules encode a CD4-IgG2 chimeric heterotetramer, and when co-expressed in the presence of CD4-kappa chimeric light chains containing the V1 and V2 domains of CD4 fused to the entire constant domain of human kappa light chains (or lambda light chains), enable the production of said heterotetramer. This heterotetramer comprises two CD4-IgG2 chimeric heavy chains and two CD4-kappa chimeric light chains. Producing heavy chains which contain the CH1 domain enables efficient association with the CD4-kappa chimeric light chains, resulting in efficient secretion of a CD4-IgG2 chimeric heterotetramer. These CD4-IgG2 chimeric heterotetramers possess increased serum half-lives and increased avidity for HIV as compared with heavy chain dimers.

SUMMARY OF THE INVENTION

This invention provides an expression vector encoding a CD4-gamma2 chimeric heavy chain homodimer. This invention also provides an expression vector encoding the heavy chains of a CD4-IgG2 chimeric heterotetramer. Finally, this invention provides an expression vector encoding the light chains of a CD4-IgG2 chimeric heterotetramer.

sequence of human CD4; V1V2, amino-terminal variable-like domains of human CD4; H, hinge region of human gamma2 heavy chain; CH2 and CH3, second and third constant regions of human gamma2 heavy chain.

FIG. 2: A) Domain structure of chimeric genes used to express CD4-IgG2 chimeric heterotetramer. Top, CD4-gamma2 chimeric heavy chain gene; Bottom, CD4-kappa chimeric light chain gene. B) Protein structure of CD4-IgG2 chimeric heterotetramer. Abbreviations: CH1—CH2—CH3, first, second and third constant regions of human gamma2 heavy chain; c-kappa, constant region of human kappa light chain.

FIGS. 3A–3F: DNA and predicted protein sequence of a CD4-gamma2 chimeric heavy chain SEQ. ID NO. 2–3 homodimer (one chain). The numbers at the end of each line indicate the nucleotide positions. The numbers above each line indicate the amino acid positions (given in single letter code). The protein domains are indicated above the sequences by arrows.

FIGS. 4A–4H: DNA and predicted protein sequence of a CD4-IgG2 chimeric heavy chain of the CD4-IgG2 chimeric heterotetramer (SEQ ID NO. 4–5). The numbers at the end of each line indicate the nucleotide positions. The numbers above each line indicate the amino acid positions (given in single letter code). The protein domains are indicated above the sequences by arrows.

FIGS. 5A–5D: DNA and predicted protein sequence of a CD4-kappa chimeric light chain of the CD4-IgG2 chimeric heterotetramer (SEQ ID NO: 6–7). The numbers at the end of each line indicate the nucleotide positions. The numbers above each line indicate the amino acid positions (given in single letter code). The protein domains are indicated above the sequences by arrows.

Figure 6:
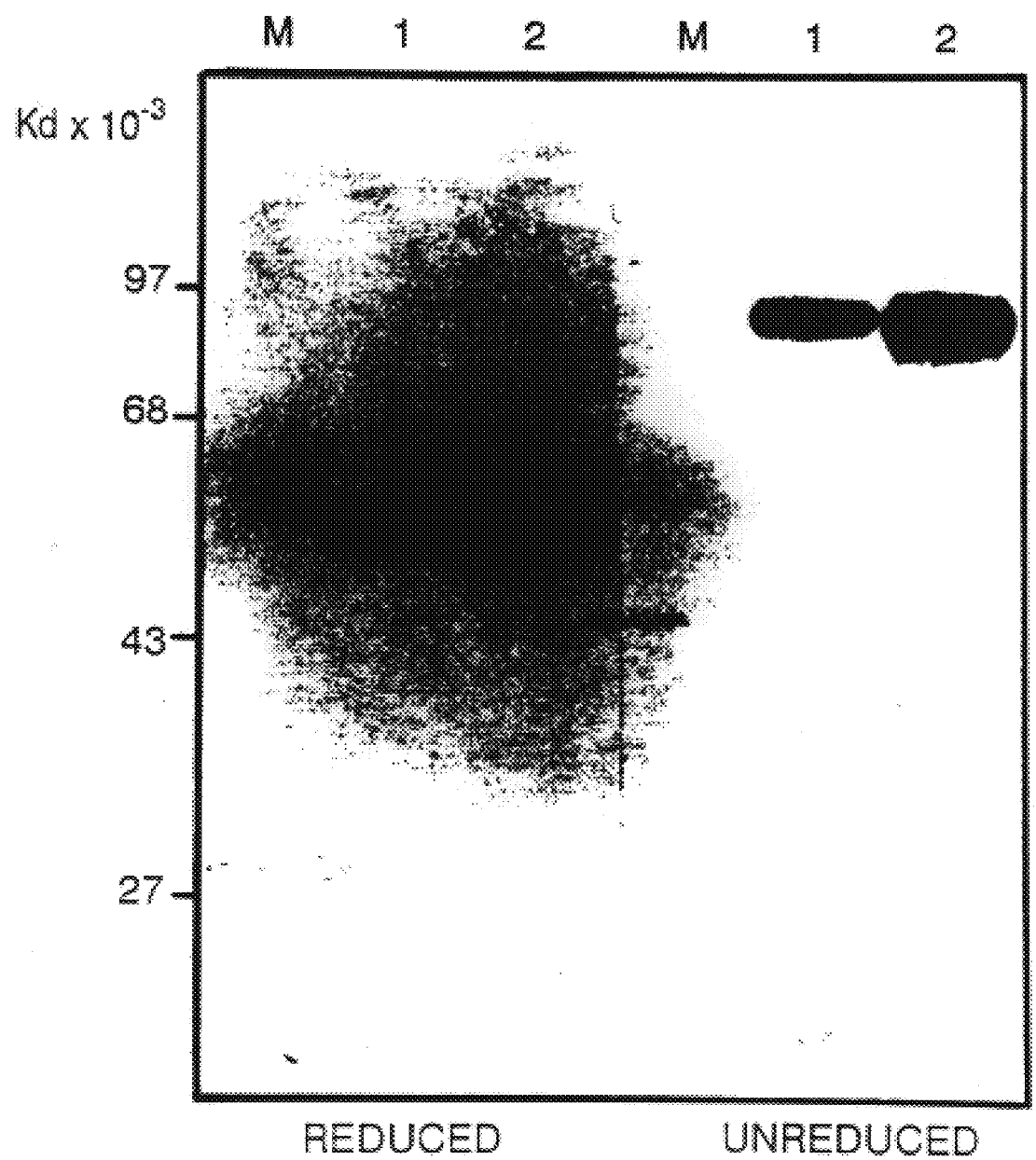

FIG. 6: Secretion of CD4-gamma2 chimeric heavy chain homodimer from transfected cells. Cos-M5 cells were mock transfected, transfected with CD4-gamma1 chimeric heavy chain mammalian expression vector DNA, or transfected with CD4-IgG2-pcDNA1. At 48–72 hours post-transfection, the cells were radiolabelled with $^{35}$S-methionine. Radiolabelled medium was precipitated with Protein-A sepharose beads. The precipitated proteins were analyzed by SDS-PAGE under reducing or non-reducing conditions and were visualized by fluorography. Lane M, medium from mock transfected cells; Lane 1, medium from cells transfected with CD4-gamma1 chimeric heavy chain mammalian expression vector DNA; Lane 2, medium from cells transfected with CD4-IgG2-pcDNA1 DNA.

Figure 7:
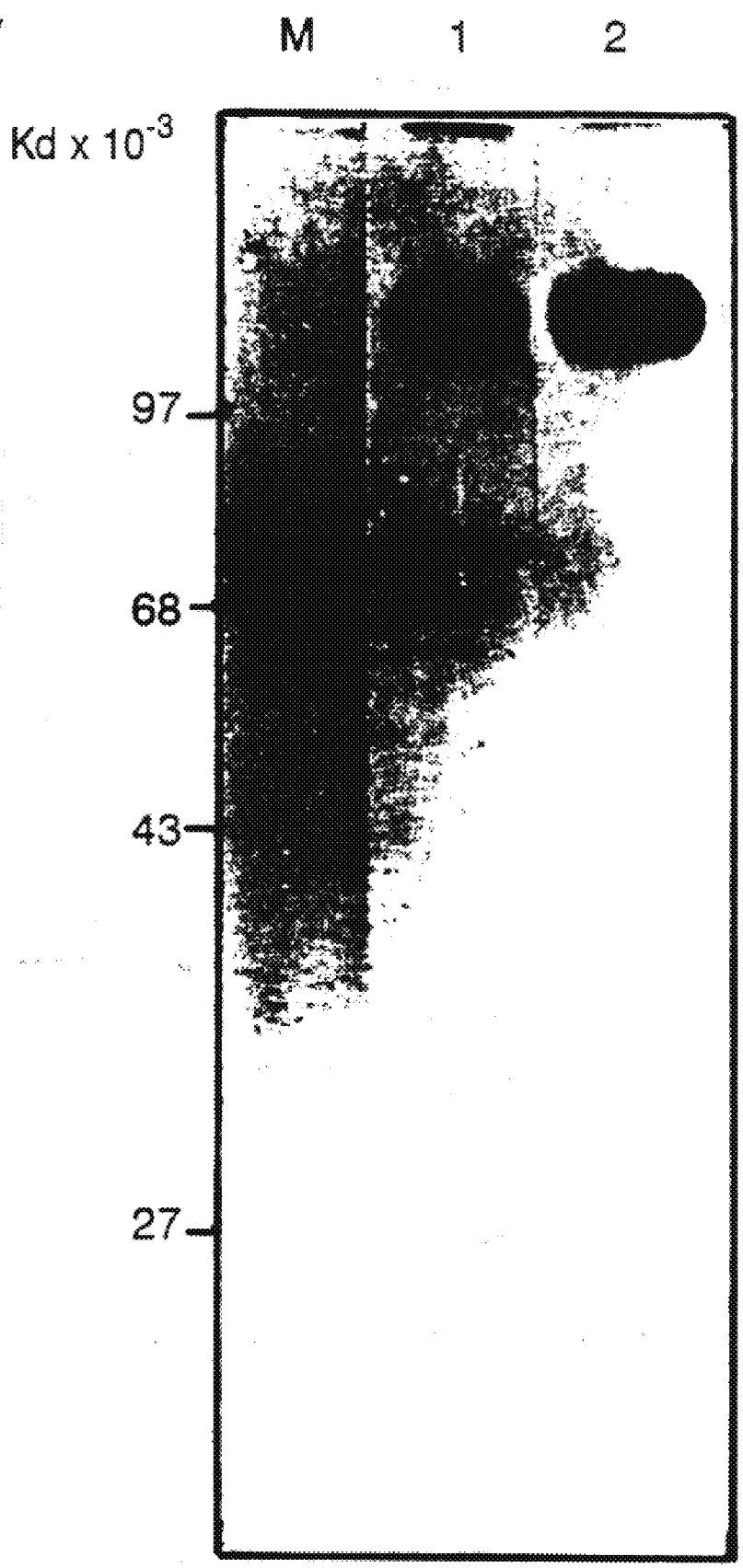

FIG. 7: Precipitation of HIV-1 gp120 with CD4-gamma2 chimeric heavy chain homodimer. Cos-M5 cells were mock transfected, transfected with CD4-gamma1 chimeric heavy chain mammalian expression vector DNA, or transfected with the CD4-IgG2-pcDNA1. At 48–72 hours post transfection, unlabelled aliquots of medium were incubated with an aliquot of $^{35}$S-methionine labelled gp120. The complexes were precipitated with Protein A-sepharose beads. The precipitates were then analyzed by SDS-PAGE followed by fluorography. Lane M, medium from mock transfected cells; Lane 1, medium from cells transfected with CD4-gamma1 chimeric heavy chain mammalian expression vector DNA; Lane 2, medium from cells transfected with CD4-IgG2-pcDNA1 DNA.

Figure 8:
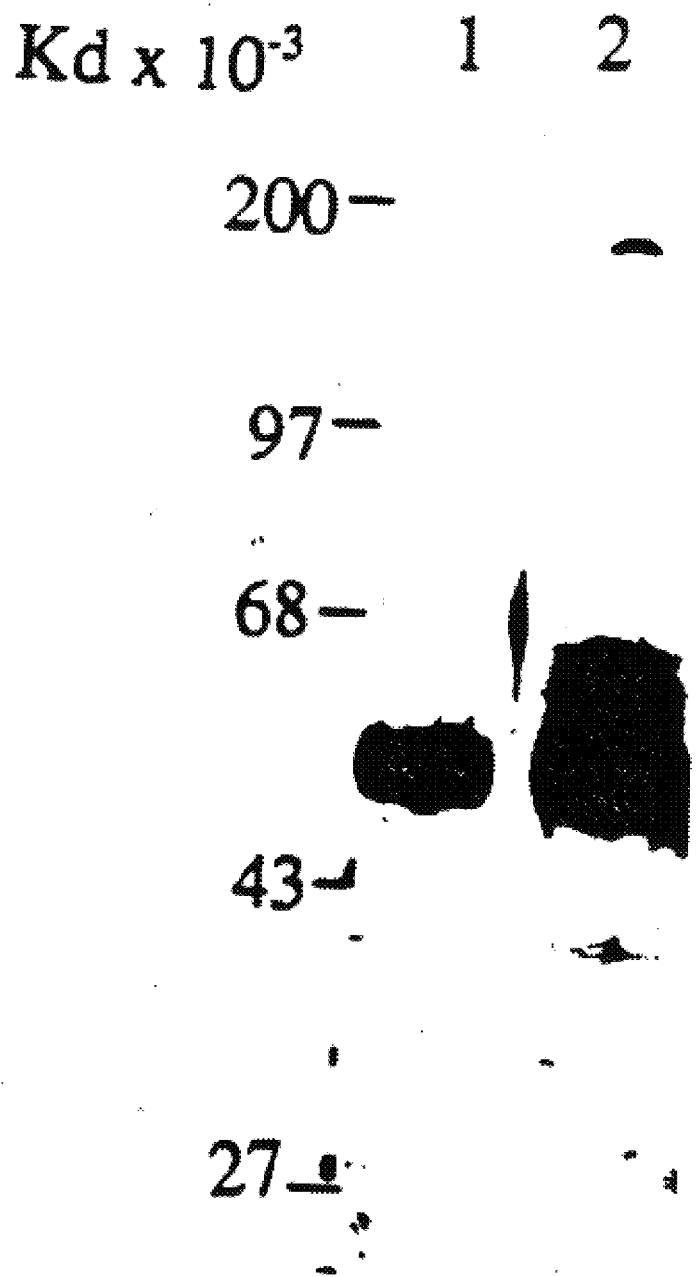

FIG. 8: Purification of CD4-gamma2 chimeric heavy chain homodimer from CHO cell-conditioned medium. Stable CHO cells constitutively secreting CD4-gamma1 chimeric heavy chain homodimer, or CD4-gamma2 chimeric heavy chain homodimer, were grown in roller bottles. Conditioned medium was passed over a Protein A-sepharose column and bound material was eluted from the column. The peak fractions were identified by SDS-PAGE followed by silver staining and pooled. The purified proteins were then analyzed by SDS-PAGE under reducing conditions followed by silver staining. Lane 1, CD4-gamma1 chimeric heavy chain homodimer; Lane 2, CD4-gamma2 chimeric heavy chain homodimer.

Figure 9:
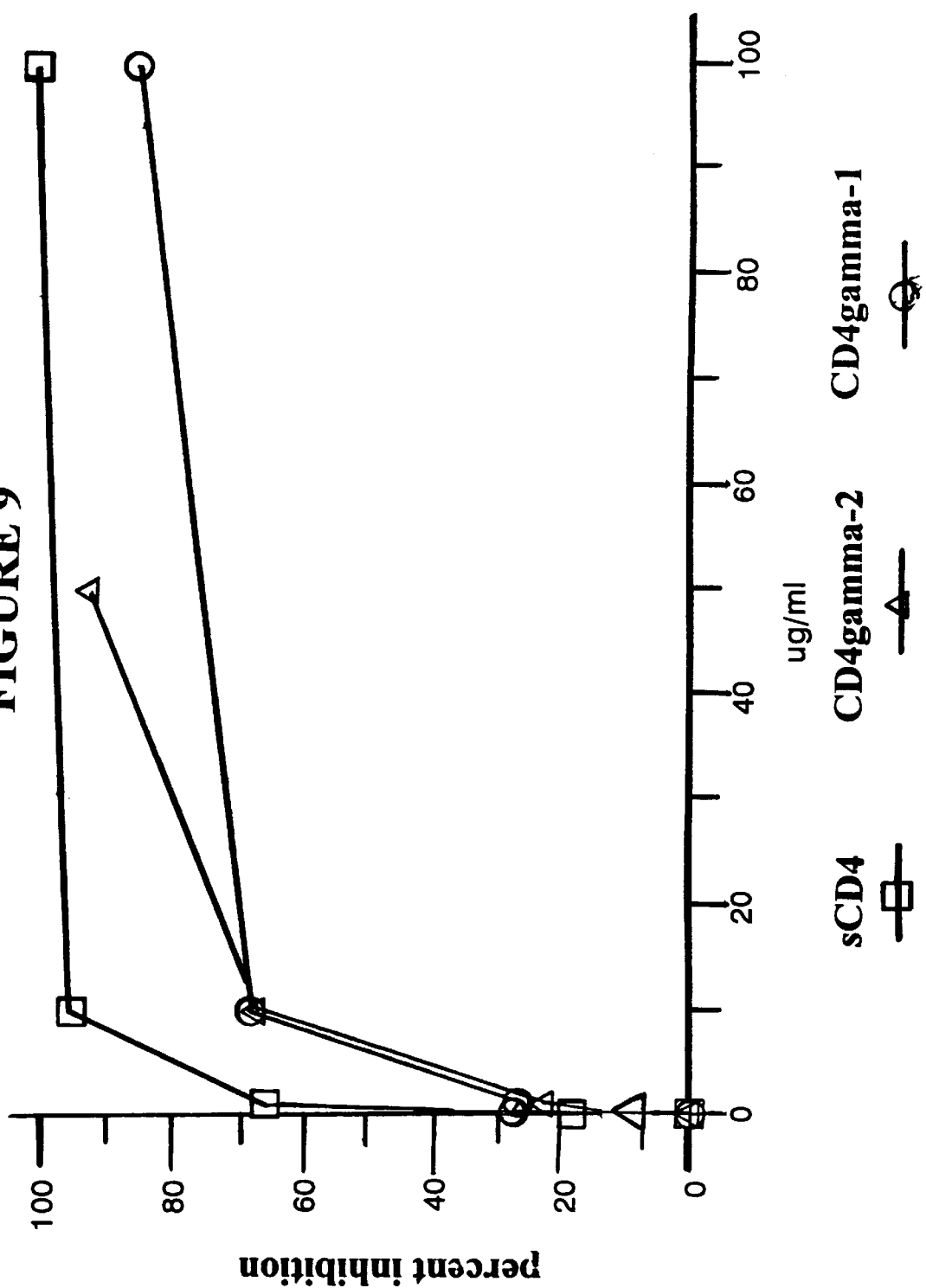

FIG. 9: Inhibition of HIV binding to CEM cells by CD4-based molecules. Soluble CD4 (sCD4), partially purified CD4-gamma1, or partially purified CD4-gamma2 were tested for inhibition of virus binding to CD4-positive cells. Bound virus was detected by indirect immunofluorescence and cytofluorography. Results are expressed as percent inhibition versus concentration of inhibiting agent.

Figure 10:
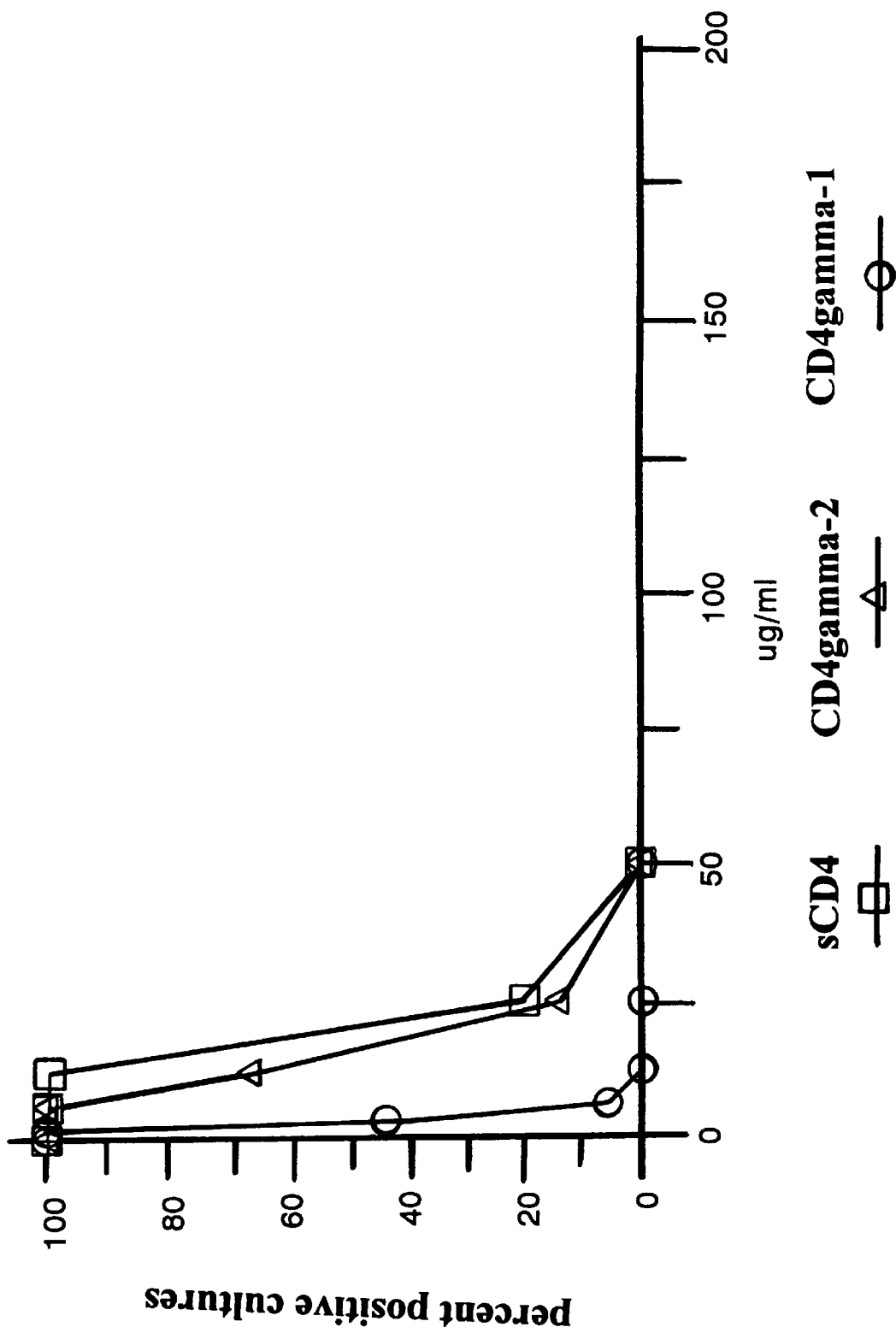

FIG. 10: Inhibition of HIV infection of CD4-positive cells by CD4-based molecules. sCD4, partially purified CD4-gamma1, or partially purified CD4-gamma2 were incubated with an HIV-1 inoculum (100 TCID$_{50}$), and mixtures were added to PHA-stimulated lymphocytes and incubated at 37° C. overnight. The cells were washed and plated in microculture ($1\times10^5$ cells/culture; 10 cultures per dilution) and monitored for reproductive viral replication by detection of HIV antigen in culture supernates 8 and 12 days later. Results are expressed as percent positive cultures at a given concentration of inhibiting agent.

Figure 11:
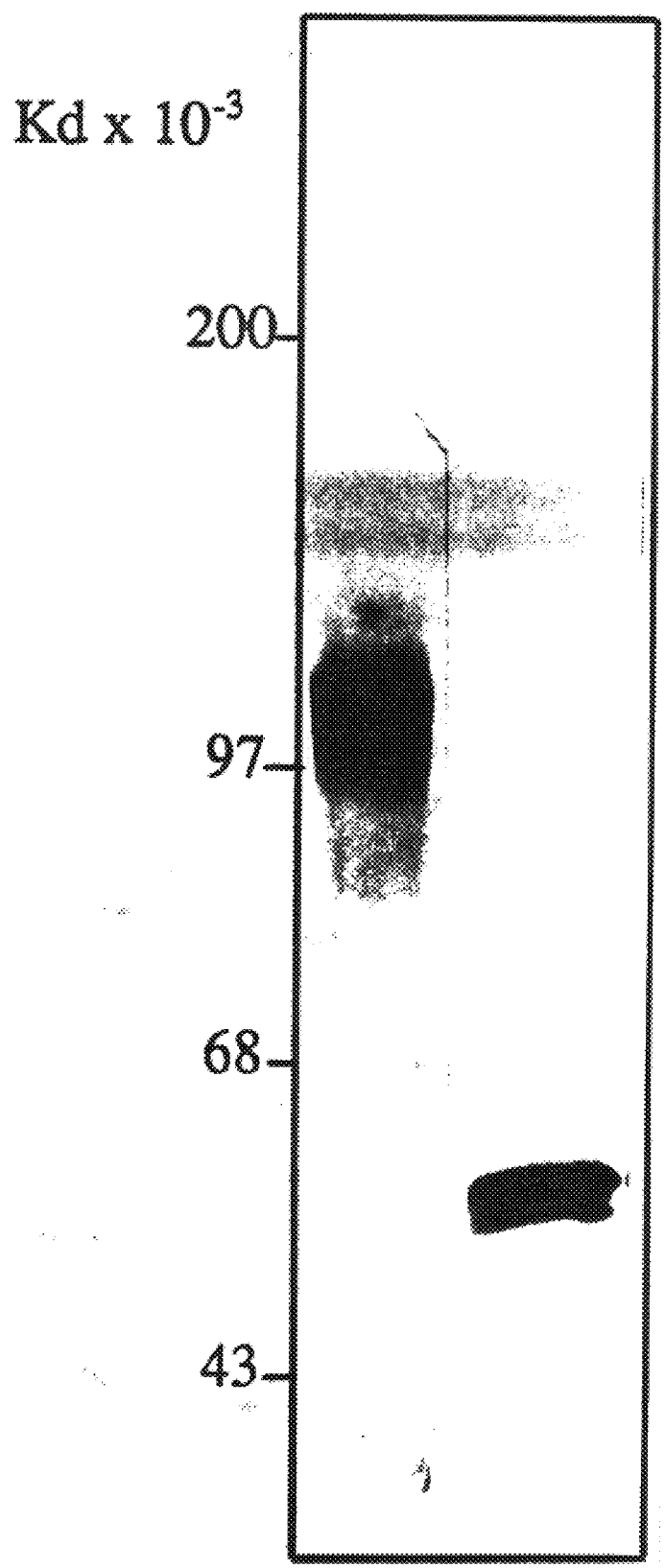

FIG. 11: Purification of CD4-gamma2 chimeric heavy chain homodimer. Stable CHO cells constitutively secreting CD4-gamma2 chimeric heavy chain homodimer were grown in roller bottles. Conditioned medium was passed over a Protein A-sepharose column and bound material was eluted from the column (see FIG. 8). The peak fractions were then pooled and passed over an S-sepharose column. After extensive washes, the CD4-gamma2 chimeric heavy chain homodimer was eluted with 50 mM BES pH 7.0, 500 mM NaCl. The peak fractions were identified by SDS-PAGE followed by silver staining, pooled, and concentrated. The pooled, concentrated CD4-gamma2 chimeric heavy chain homodimer was then applied to a Sephacryl S-300HR column preequilibrated and run with PBS. The peak fraction corresponding to purified CD4-gamma2 chimeric heavy chain homodimer was identified by SDS-PAGE followed by silver staining. The peak fractions were then pooled and concentrated. The purified protein was then analyzed by SDS-PAGE under non-reducing and reducing conditions followed by silver staining. Lane 1: approximately 1.5 μg protein run under non-reducing conditions, Lane 2: approximately 1.5 μg protein run under reducing conditions.

FIG. 12: Secretion of CD4-IgG2 chimeric heterotetramer from stably transfected cells. CHO cells stably expressing both CD4-IgG2 chimeric heavy chains and CD4-kappa chimeric light chains were radiolabelled with $^{35}$S-methionine and cysteine. Radiolabelled medium was precipitated with Protein-A sepharose beads. (A) The precipitated proteins were analyzed by SDS-PAGE under non-reducing conditions, and were visualized by fluorography. Lane 1: medium from untransfected CHO cells, Lane 2: medium from cells stably expressing both the CD4-IgG2 chimeric heavy chains, and CD4-kappa chimeric light chains. (B) An identical sample to that run in lane 2 from (A) was run on SDS-PAGE under non-reducing conditions. The lane from this SDS-PAGE gel was excised and the proteins reduced by incubation of the gel slice for 45 minutes at 4° C. in equilibration buffer (62.5 mM TrisHCl pH 6.8, 2.3% SDS 5% β-mercaptoethanol, 10% glycerol). After incubation of the gel slice under reducing conditions, the proteins contained within the gel were analyzed by SDS-PAGE and visualized by fluorography.

Figure 13:
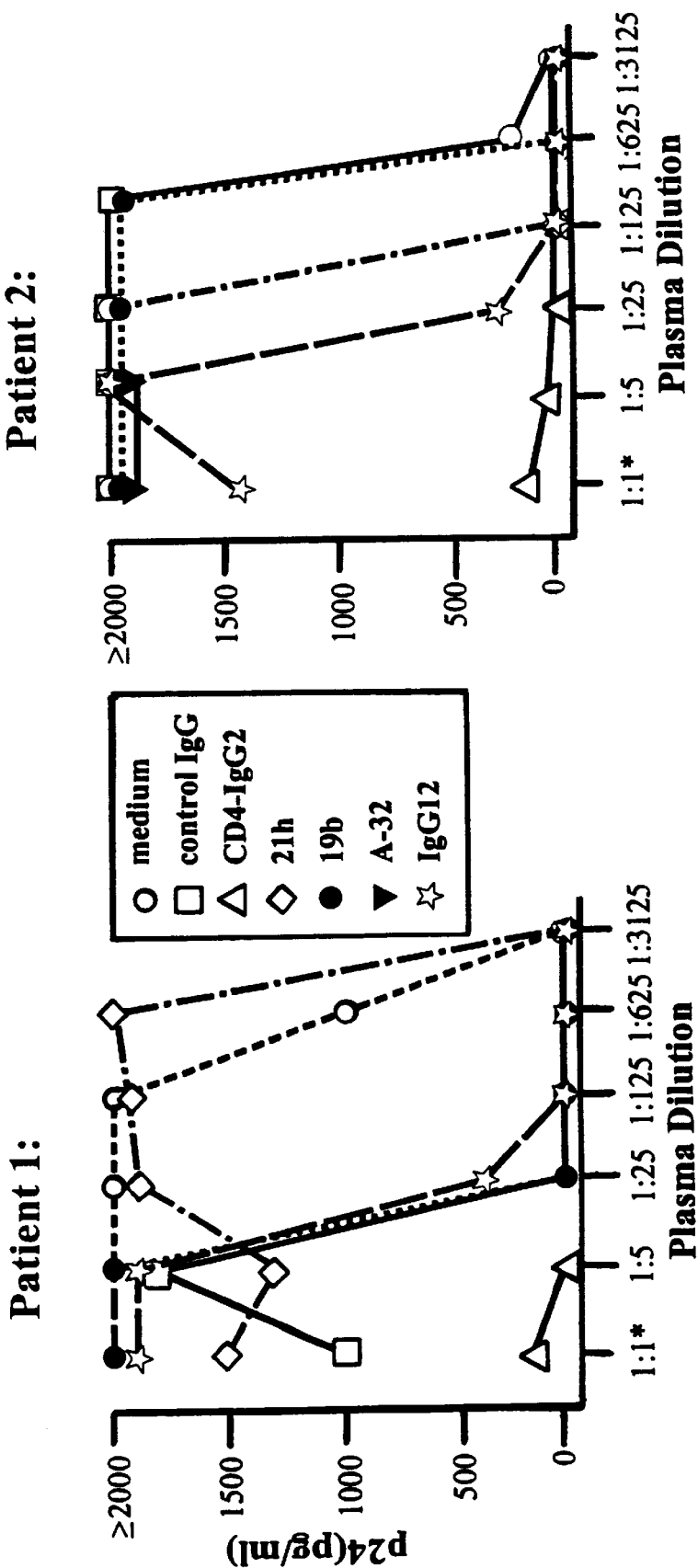

FIG. 13: Ex vivo neutralization of clinical HIV-1 isolates in plasma of infected individuals by CD4-IgG2 and monoclonal antibodies. *undiluted plasma.

Figure 14:
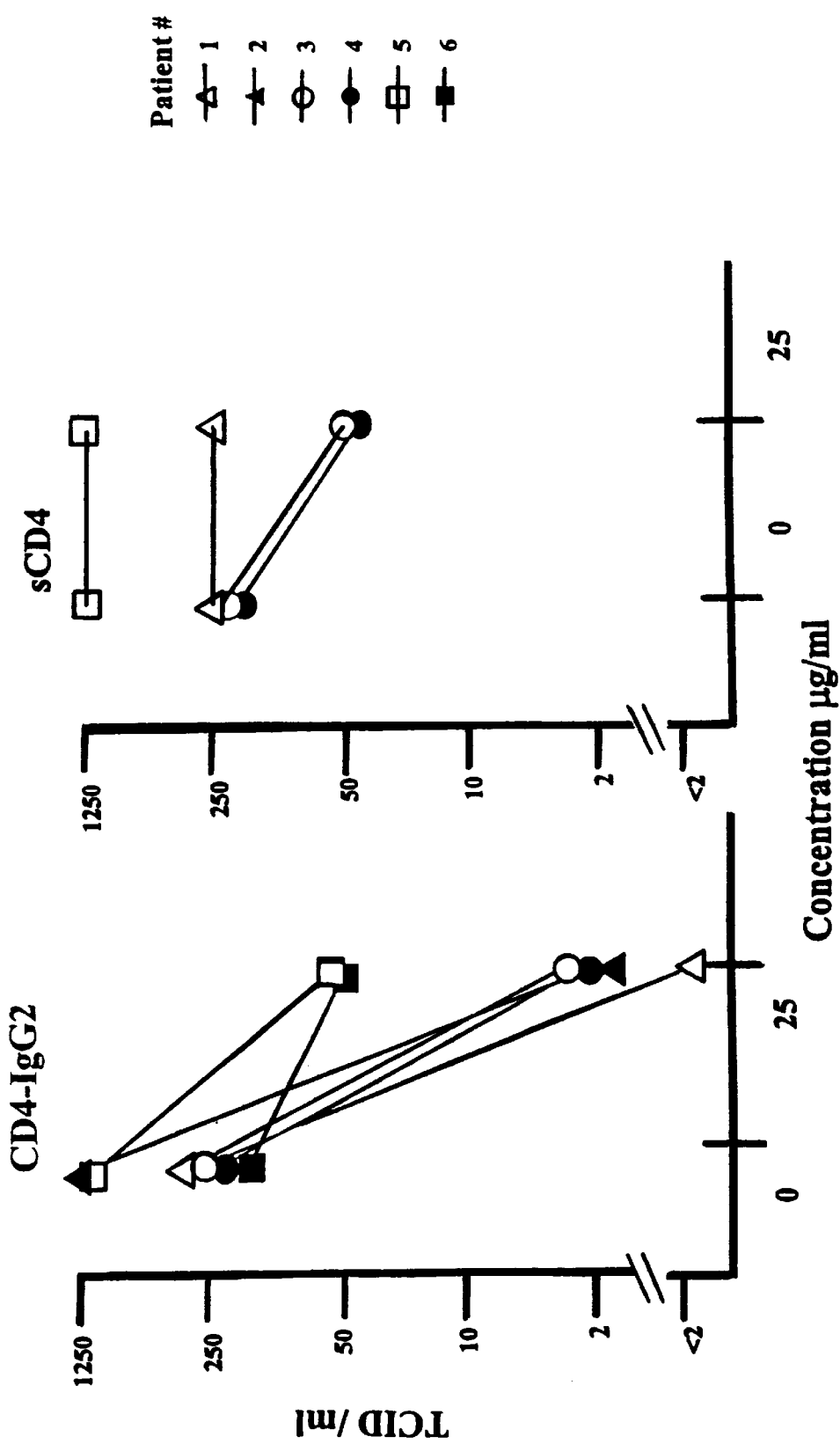

FIG. 14: Ex vivo neutralization of clinical HIV-1 isolates in plasma of infected individuals by CD4-IgG2 and sCD4.

DETAILED DESCRIPTION OF THE INVENTION

Five expression vectors and two plasmids designated CD4-IgG2-Rf, CD4-IgG1-Rf, CD4-IgG1HC-pRcCMV, CD4-IgG2HC-pRcCMV, CD4-kLC-pRcCMV, CD4-IgG1-pcDNA1, and CD4-IgG2-pcDNA, respectively have been deposited with the American Type Culture Collection, Rocksville, Md., U.S.A. 20852, under ATCC Accession Nos. 40949, 40950, 75192, 75193, 75194, 40951, and 40952, respectively. These deposits were made pursuant to the provisions of the Budapest Treaty on the International Recognition of the Deposit of Microorganisms for the Purposes of Patent Procedure (Budapest Treaty).

Specifically, the invention provides an expression vector designated CD4-IgG2-pcDNA1 (ATCC No. 40952) encoding a CD4-gamma2 chimeric heavy chain homodimer. The invention additionally provides a CD4-gamma2 chimeric heavy chain homodimer encoded by this expression vector or any other expression vector having the same DNA coding region inserted therein. Specifically, the invention also provides expression vectors designated CD4-IgG2HC-pRcCMV (ATCC No. 75193), and CD4-kLC-pRcCMV (ATCC No. 75194), encoding a CD4-IgG2 chimeric heavy chain and a CD4-kappa chimeric light chain. The invention additionally provides a CD4-IgG2 chimeric heterotetramer encoded by these expression vectors or any other expression vector having the same DNA encoding region inserted therein.

In accordance with the invention, numerous vector systems for expression may be employed. For example, one class of vectors utilizes DNA elements which are derived from animal viruses such as bovine papilloma virus, polyoma virus, adenovirus, vaccinia virus, baculovirus, retroviruses (RSV, MMTV or MOMLV) or SV40 virus. Additionally, cells which have stably integrated the DNA into their chromosomes may be selected by introducing one or more markers which allow selection of transfected host cells. The marker may provide for prototrophy to an auxotrophic host, biocide resistance, e.g., antibiotics, or resistance to heavy metals such as copper or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals. The cDNA expression vectors incorporating such elements include those described by Okayama. (37)

Thus, the invention further provides a method of producing a CD4-gamma2 chimeric heavy chain homodimer. This method comprises
  a) transfecting a mammalian cell with an expression vector for producing the CD4-gamma2 chimeric heavy chain homodimer;
  b) culturing the resulting transfected mammalian cell under conditions such that CD4-gamma2 chimeric heavy chain homodimer is produced; and
  c) recovering the CD4-gamma2 chimeric heavy chain homodimer so produced.

Once the vector or DNA sequence containing the constructs has been prepared for expression, the expression vectors may be transfected or introduced into an appropriate mammalian cell host. Various techniques may be employed such as protoplast fusion, calcium phosphate precipitation, electroporation or other conventional techniques. In the case of protoplast fusion, the cells are grown in media and screened for the appropriate activity. Expression of the gene(s) results in production of the fusion protein which corresponds to one chain of the CD4-gamma2 chimeric heavy chain homodimer. The fusion protein may then be treated to form the chimeric heavy chain homodimer.

Further, methods and conditions for culturing the resulting transfected cells and for recovering the chimeric heavy chain homodimer so produced are well known to those skilled in the art and may be varied or optimized depending upon the specific expression vector and mammalian host cell employed.

In accordance with the claimed invention, the preferred host cells for expressing the chimeric heavy chain homodimers of this invention are mammalian cell lines, including, for example, monkey kidney CV1 line transformed by SV40 (COS-7); human embryonic kidney line 293; baby hamster kidney cells (BHK); Chinese hamster ovary-cells-DHFR (CHO); monkey kidney cells (CV1); African green monkey kidney cells (VERO-76); human cervical carcinoma cells (HELA); canine kidney cells (MDCK); human lung cells (W138); human liver cells (Hep G2); mouse mammary tumor (MMT 060562); mouse cell line (C127) and myeloma cell lines.

The invention further provides a method of inhibiting the HIV infection of a CD4+ cell which comprises treating the CD4+ cell with the CD4-gamma2 chimeric heavy chain homodimer in an amount which is effective to inhibit infection of the cell.

Additionally, the invention provides a method of preventing a subject from being infected with HIV which comprises administering to the subject the CD4-gamma2 chimeric heavy chain homodimer in an amount which is effective to prevent the subject from being infected with HIV.

Although the invention encompasses the administration of the chimeric heavy chain homodimer to various subjects, AIDS patients are of particular interest. Further, methods of administering the homodimer are well known in the art and include, merely by way of example, subcutaneous, intramuscular and intravascular injection, alone or in combination with other agents such as AZT or DDI.

Further provided is a method of treating a subject infected with HIV so as to block the spread of HIV infection which comprises administering to the subject an amount of the CD4-gamma2 chimeric heavy chain homodimer in an amount which is effective to block the spread of HIV infection.

For example, the homodimer may be administered to patients having HIV infection at a dosage capable of maintaining a concentration of greater than about 100 ng of CD4-gamma2 chimeric heavy chain homodimer/ml plasma. For CD4-gamma2 chimeric heavy chain homodimer variants having different molecular weights, about 2 picomoles of soluble receptor per ml of plasma, an amount for example, sufficient to establish a stoichiometric equivalence with native (membrane bound) and soluble receptor is administered. Typically, the dosage of soluble CD4 is about 100 $\mu$g/kg of patient weight/day.

The foregoing method may be used to help prevent the spread of the HIV virus within the body of a HIV infected patient. Additionally, CD4-gamma2 chimeric heavy chain homodimer may be administered as a prophylactic measure to render a subject's blood less susceptible to the spread of the HIV virus. Such prophylactic administration includes administration both prior to HIV contact or shortly thereafter, or both.

A pharmaceutical composition which comprises the CD4-gamma2 chimeric heavy chain homodimer of thus invention in an amount effective to inhibit HIV infection of a CD4+ cell and a pharmaceutically acceptable carrier is further provided.

Pharmaceutically acceptable carriers are well known in the art to which the present invention pertains and include, but are not limited to, 0.01–0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservations and other additives may also be present, such as, for example, antimicrobials, antioxidants, chelating agents, inert gases and the like. (38)

The invention further provides a composition of matter comprising a CD4-gamma2 chimeric heavy chain homodimer and a toxin linked thereto.

Some example of toxins are the deglycosylated A chain of ricin, domains II or III of Pseudomonas exotoxin A, Diphtheria toxin, or a non-peptidyl cytotoxin. These toxins may be linked using conventional in vitro protein cross-linking agents (39–41). Additionally the toxins may be linked by recombinant synthesis as a fusion protein (see for example U.S. Pat. No. 4,765,382).

The invention also provides a diagnostic reagent comprising a CD4-IgG2 chimeric heavy chain homodimer and a detectable marker linked thereto. By employing a molecule which binds to the HIV virus and additionally has attached to it a detectable marker, one may identify cells which are infected with HIV. Examples of conventional detectable markers includes radioisotopes such as I125, chromophores, and fluorophores.

Thus, the chimeric heavy chain homodimer of the invention may be used in an assay for HIV or SIV viral infection in a biological sample by contacting a sample derived from an animal suspected of having HIV or SIV infection, with the homodimer of the invention, and detecting whether a complex forms with gp120, either alone or on the surface of an HIV-infected cell. For this purpose the homodimer may be labeled with a detectable marker or may be unlabeled and then be detected with another reagent which is detectably labeled and is specifically directed to the homodimer or to a complex between it and gp120.

For example, a biological sample may be treated with nitro-cellulose, or another solid support which is capable of immobilizing cells, cell particles or soluble protein. The support may then be washed with suitable buffers followed by treatment with the chimeric heavy chain homodimer which may be detectably labeled. The solid phase support may then be washed with buffer a second time to remove unbound fusion protein and the labeled homodimer detected.

In carrying out the assay the following steps may be employed.

a) contacting a sample suspected of containing gp120 with a solid support to effect immobilization of gp120, or cells which express gp120 on their surface;

b) contacting said solid support with the detectably labeled chimeric heavy chain homodimer of the invention;

c) incubating said detectably labeled homodimer with said support for a sufficient amount of time to allow the homodimer to bind to the immobilized gp120 or cell which expresses gp120 on its surface;

d) separating the solid phase support from the incubation mixture obtained in step c); and e) detecting bound labeled homodimer and thereby detecting gp120.

Such a method may be formatted either as a qualitative or as a quantitative test using methods well known in the art.

Alternatively, labeled homodimer-gp120 complex may be separated from a reaction mixture by contacting the complex with an immobilized antibody or protein which is specific for an immunoglobulin or, e.g., protein A, protein G, or anti-IgG antibodies. Such anti-immunoglobulin antibodies may be monoclonal or polyclonal. The solid support may then be washed with suitable buffers to obtain an immobilized gp-120-labeled homodimer-antibody complex. The label on the homodimer may then be detected so as to measure endogenous gp120, and thereby detect the presence of HIV.

In one embodiment of the invention, a method for detecting HIV or SIV viral infection in a sample is provided comprising:

a) contacting a sample suspected of containing gp120 with a CD4-gamma2 chimeric heavy chain homodimer in accordance with this invention, and the Fc portion of an immunoglobulin chain; and b) detecting whether a complex is formed.

The invention also provides a method of detecting gp120 in a sample comprising:

a) contacting a mixture obtained by contacting a sample suspected of containing gp120 with a homodimer of this invention, and the Fc portion of an immunoglobulin chain, with an Fc binding molecule, such as an antibody, protein A, or protein G, which is immobilized on a solid phase support and is specific for the homodimer, to obtain a gp120-homodimer immobilized antibody complex, b) washing the solid phase support obtained in step (a) to remove unbound homodimer; and c) detecting the homodimer.

Of course, the specific concentrations of unlabeled or detectably labeled homodimer and gp120, the temperature and time of incubation, as well as other assay conditions, may be varied depending on various factors including the concentration of gp120 in the sample, the nature of the sample, and the like. Those skilled in the art are readily able to determine operative and optimal assay conditions for each determination.

Also provided is an enzyme-linked immunoadsorbent assay (ELISA) to detect and quantify soluble CD4 (sCD4) or CD4 chimeric proteins. In carrying out the assay, the process comprises:

a) contacting a sample containing sCD4 with a solid support to immobilize soluble sCD4;

b) contacting said solid support with the detectably labeled monoclonal antibody OKT4a alone, or with a sample containing sCD4 or CD4 chimeric proteins and OKT4a;

c) incubating said detectably labeled OKT4a containing media for sufficient time to allow for binding to immobilized SCD4;

d) separating the solid phase support from the incubation mixture in step (c);

e) detecting the bound OKT4a and thereby quantifying the amount of CD4 contained in the sample.

The invention further provides an expression vector encoding the heavy chains of a CD4-IgG2 chimeric heterotetramer, designated CD4-IgG2HC-pRcCMV (ATTC No. 75193). The invention also provides a CD4-IgG2 chimeric heterotetramer, the heavy chains of which are encoded by this expression vector or another vector containing the same coding sequence.

Additionally, the invention provides an expression vector encoding the light chains of a CD4-IgG2 chimeric heterotetramer, designated CD4-kLC-pRcCMV (ATTC No. 75194). Finally, the invention provides a CD4-IgG2 chimeric heterotetramer, the light chains of which are encoded by the CD4-kLC-pRcCMV expression vector or another vector containing the same coding sequences.

Further, the invention provides a CD4-IgG2 chimeric heterotetramer both the heavy and light chains of which are encoded by the aforementioned expression vectors.

The invention further provides a method of producing such a CD4-IgG2 chimeric heterotetramer. This method comprises:

a) cotransfecting a mammalian cell with the expression vector for producing the light chains of a CD4-IgG2 chimeric heterotetramer and an expression vector encoding a light chain;

b) culturing the resulting cotransfected mammalian cell under conditions such that CD4-IgG2 chimeric heterotetramer is produced; and c) recovering the CD4-IgG2 chimeric heterotetramer so produced.

Methods of cotransfecting mammalian cells are well known in the art and include those discussed hereinabove. Similarly, expression vectors encoding light chains are well known in the art.

The invention additionally provides a method of producing a CD4-IgG2 chimeric heterotetramer which comprises:

a) cotransfecting a mammalian cell with the expression vector for producing the light chains of a CD4-IgG2 chimeric heterotetramer and with an expression vector encoding an IgG1 heavy chain;

b) culturing the resulting cotransfected mammalian cell under conditions such that a CD4-IgG2 chimeric hetero-tetramer is produced; and c) recovering the CD4-IgG2 chimeric heterotetramer so produced.

Further the invention provides a method of producing an CD4-IgG2 chimeric heterotetramer which comprises:

a) cotransfecting a mammalian cell with the expression vector for producing the heavy chains of a CD4-IgG2 chimeric heterotetramer and an expression vector for producing the light chains of an CD4-IgG2 chimeric heterotetramer;

b) culturing the resulting cotransfected mammalian cell under conditions such that the CD4-IgG2 chimeric heterotetramer is produced; and c) recovering the CD4-IgG2 chimeric heterotetramer so produced.

The invention also includes a method of inhibiting HIV infection of a CD4+ cell which comprises treating the CD4+ cell with either a CD4-IgG2 chimeric heterotetramer, the heavy chains of which are encoded by the expression vector designated CD4-IgG2HC-pRcCMV; a CD4-IgG2 chimeric heterotetramer, the light chains of which are encoded by the expression vector designated CD4-kLC-pRcCMV; or a CD4-IgG2 chimeric heterotetramer, both the heavy and the light chains of which are encoded by both of the above expression vectors, in an amount effective to inhibit infection of the cell.

The invention further being a method of preventing a subject from being infected with HIV. This method comprises administering to the subject either a CD4-IgG2 chimeric heterotetramer, the heavy chains of which are encoded by the expression vector designated CD4-IgG2HC-pRcCMV; a CD4-IgG2 chimeric heterotetramer, the light chains of which are encoded by the expression vector designated CD4-kLC-pRcCMV; or a CD4-IgG2 chimeric heterotetramer, both the heavy and the light chains of which are encoded by the above expression vectors, in an amount which is effective to prevent the subject from being infected with HIV.

The invention also provides a method of treating a subject infected with HIV so as to block the spread of HIV infection. This method comprises administering to the subject either a CD4-IgG2 chimeric heterotetramer, the heavy chains of which are encoded by the expression vector designated CD4-IgG2HC-pRcCMV; a CD4-IgG2 chimeric heterotetramer, the light chains of which are encoded by the expression vector designated CD4-kLC-pRcCMV; or a CD4-IgG2 chimeric heterotetramer, both the heavy and the light chains of which are encoded by the above-described expression vectors, in an amount effective to block spread of HIV infection, for example, within the subject or an AIDS patients body.

The invention also provides a pharmaceutical composition which comprises either a CD4-IgG2 chimeric heterotetramer, the heavy chains of which are encoded by the expression vector designated CD4-IgG2HC-pRcCMV; a CD4-IgG2 chimeric heterotetramer, the light chains of which are encoded by the expression vector designated CD4-kLC-pRcCMV, or a CD4-IgG2 chimeric heterotetramer, both the heavy and the light chains of which are encoded by the above-described expression vectors, in an amount effective to inhibit HIV infection of a CD4+ cell, and a pharmaceutically acceptable carrier.

Further provided by the invention is a composition of matter comprising either a CD4-IgG2 chimeric heterotetramer, the heavy chains of which are encoded by the expression vector designated CD4-IgG2HC-pRcCMV; a CD4-IgG2 chimeric heterotetramer, the light chains of which are encoded by the expression vector designated CD4-kLC-pRcCMV, or a CD4-IgG2 chimeric heterotetramer, both the heavy and the light chains of which are encoded by the above-described expression vectors, and a toxin linked thereto.

In one embodiment of the invention, the toxin is the deglycosylated A chain of ricin, domains II or III of Pseudomonas exotoxin A, Diptheria toxin, or a non-peptidyl cytotoxin.

The invention further provides a diagnostic reagent either comprising a CD4-IgG2 chimeric heterotetramer, the heavy chains of which are encoded by the expression vector designated CD4-IgG2HC -pRcCMV; a CD4-IgG2 chimeric heterotetramer the light chains of which are encoded by the expression vector designated CD4-kLC-pRcCMV; or a CD4-IgG2 chimeric heterotetramer both the heavy and light chains and a detectable marker linked thereto. Examples of suitable detectable markers are radioisotopes, chromophores or fluorophores.

In order to facilitate understanding of the following examples, certain frequently occurring methods and/or terms are best described in Maniatis et al. (42).

This invention illustrates in the Experimental Details section which follows. These sections are set forth to aid in an understanding of the invention but are not intended to, and should not be construed to, limit in any way the invention as set forth in the claims which follow thereafter.

Experimental Details

A. Materials and Methods

Figure 1A:
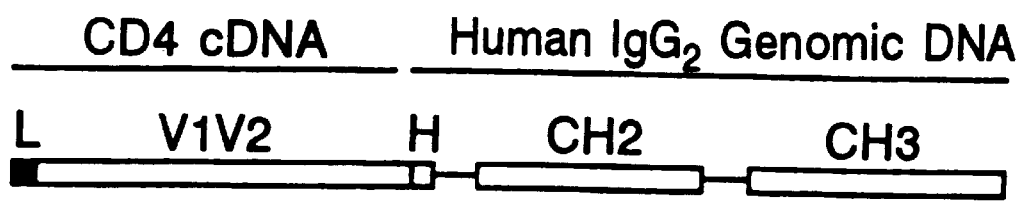
FIG. 1: A) Domain structure of CD4-gamma2 chimeric heavy chain gene; B) Protein structure of CD4-gamma2 chimeric heavy chain homodimer. The sequence shown below is the single letter amino acid code of the junction between CD4 (phe179) and the hinge region of human gamma2 heavy chain (SEQ ID NO:1) Note that the hinge region of a gamma2 heavy chain contains four cysteines (see text for discussion). Abbreviations: L, leader (signal)

1. Construction of CD4-gamma2 chimeric heavy chain gene encoding CD4-gamma2 chimeric heavy chain homodimer:

The human CD4 cDNA was excised from the plasmid pSP6T4 (4) as an EcoR1/Stu1 restriction fragment. The 0.70 kilobase fragment was isolated and cloned into EcoR1/Sma1 digested M13mp18. This intermediate vector (M13m18 (CD4)) was then isolated, linearized with Pst1, purified, and treated with Bacterial Alkaline Phosphatase (BAP). The 2.0 Kb Pst1/PstB1 fragment form the plasmid pBr gamma2 containing the human gamma2 heavy chain (36) (containing the hinge, CH2, and CH3 exons) was isolated and cloned into the BAP-treated M13mp18 CD4 vector. Resulting recombinants were then screened for the correct orientation of the Pst1 fragment (with respect to the CD4 sequence) to obtain a vector which contains in tandem CD4 (EcoR1/Stu1)—gamma2 (Pst1/Pst1). to obtain a CD4-gamma2 chimeric heavy chain gene, oligonucleotide-mediated site-directed mutangenesis was performed to juxtapose the CD4 and gamma2 heavy chain DNA sequences, ligating the CD4 sequence in frame to the hinge exon. The resulting chimeric DNA molecule encodes a protein containing the V1V2 domains of CD4 followed by the hinge, CH2m and CH3 domains of gamma2 heavy chain (FIG. 1A). Mutangenesis was performed on single-stranded DNA isolated from recombinant phage from transformed TG1 cells (Amersham). Briefly, template DNA was annealed with a 34-mer oligonucleotide (5'-GACACAACATTTGCGCTCGAAAGCTAGCACCACG-3', SEQ. ID. NO. 8), containing sequences which join the last codon encoding Phe (179) form V1V2 of CD4 to the first codon of the hinge for IgG2 (encoding Glu) (FIGS. 1A and 3). After second strand synthesis, double stranded DNA was transformed into competent TG1 cells. Isolated plaques were then grown in fresh TG1 cells and single stranded DNA was purified for DNA sequencing. All mutations were verified and confirmed by dideoxy sequencing using the Sequenase system (USB). Plaques containing the chimeric gene with the correct sequence were then grown in TG1 cells, and Rf DNA (designated CD4-IgG2-Rf) was isolated from the cells.

2. Construction of Mammalian Expression Vector Encoding CD4-gamma2 chimeric heavy chain homodimer:

The CD4-gamma2 chimeric heavy chain gene was isolated from the recombinant Rf DNA following Rf linearization with EcoR1. The EcoR1 sites in the linearized DNA were filled in with the Klenow fragment of DNA polymerase I. The flush ended DNA was then ligated overnight at 15 degrees Celsius with T4 DNA ligase to a 100-fold molar excess of HindIII linkers. After heat inactivation of T4 DNA ligase for 15 minutes at 70 degrees Celsius, the HindIII-linkered DNA was extensively digested with HindIII to liberate a fragment containing the CD4-gamma2 chimeric heavy chain gene. This HindIII fragment was then purified and ligated to the expression vector pcDNA-1 (Invitrogen), which was previously digested with HindIII and BAP treated. The resulting plasmid was then transformed into MC1061. P3 cells. Plasmid DNA was isolated from recombinant clones, and verification of the presence of the HindIII insert and orientation of the insert with respect to the cytomegalovirus (CMV) promoter in the plasmid was made by restriction enzyme analysis. The resulting mammalian expression plasmid which encodes a CD4-gamma2 chimeric heavy chain homodimer is designated CD4IgG2-pcDNA1.

3. Expression of CD4-IgG2-pcDNA1 in mammalian cells:

a. Transient Expression

CosM5 cells grown in DMEM containing 10% fetal calf serum were split to 75% confluence. On the following day, the cells were transfected for 16–20 hours with 10 micrograms of CaCl-purified plasmid CD4IgG2-pcDNA1 DNA by the stranded CaPO (4) precipitation technique. After transfection, fresh medium was added to the cells. Analysis of the products synthesized 48–72 hours post-transfection was performed by radiolabelling of transfectants with $^{35}$S-methionine for 12–18 hours followed by precipitation of media and cell lysates using anti-CD4 antibodies or by incubation with Protein A-sepharose beads alone followed by SDS-PAGE under reducing or non-reducing conditions (FIG. 6). In addition, analysis of media and cell lysates was performed 48–72 hours post-transfection by standard Western blotting procedures.

b. Stable Expression

Dhfr-Chinese hamster ovary cells (CHO) were transfected with 20 mircograms of CsCl purified DNA in a 1000:1 molar ratio of CD4IgG2-pcDNA1:p410 (p410 is an expression plasmid containing the dhfr gene), although other ratios may also be used. Approximately 3–5 post-transfection, cells were placed in selective medium (nucleoside-free alpha MEM containing 10% dialyzed fetal calf serum). Approximately 10–15 days post-selection, individual cell clones were picked and analyzed for stable expression of CD4-gamma2 chimeric heavy chain homodimer by several screening techniques, such as ELISA and precipitation with Protein A-sepharose beads followed by SDS-PAGE under reducing and non-reducing conditions. Clones expressing the highest levels were subjected to successive rounds of amplification of the newly introduced DNA sequences in increasing concentrations of methotrexate. Stable CHO cell lines were thus generated which secrete between 10–100 micrograms/milliliter of CD4-gamma2 chimeric heavy chain homodimer.

4. Purification of CD4-gamma2 chimeric heavy chain homodimer from CHO conditioned media:

CD4-gamma2 chimeric heavy chain homodimer was purified in a single step using Protein A-Sepharose column chromatography. CHO cells secreting CD4-gamma2 chimeric heavy chain homodimer were grown to high density in roller bottles in medium containing alpha MEM with 10% IgG-free fetal calf serum. Conditioned media was collected, clarified by centrifugation, and diluted 1:1 with PBS with/or without detergent (i.e. Tween) in this and subsequent buffers. The diluted media was then applied to a 5 ml column of Protein A-Sepharose first flow previously equilibrated with PBS, at a flow rate of 60 ml/hour. After extensive washing, the specifically bound material was eluted with 100 mM glycine/HCl, pH 3.5, directly into an aliquot of 1 M Tris.HCl pH 8.0 to immediately neutralize the eluted fractions. The fractions were then analyzed by SDS-PAGE under reducing and non-reducing conditions followed by silver staining and pooled (FIG. 8).

The pooled fractions were then applied to a 10 ml column of S-sepharose fast flow previously equilibrated with 50 mM BES pH 7.0 at a flow rate of 120 ml/hr. After application of sample, a step elution gradient (consisting of the following 4 steps: 5 column volumes of 50 mM BES pH 7.0, 4 column volumes of 50 mM BES pH 7.0, 100 mM NaCl, 6 column volumes of 50 Mm BES pH 7.0 225 mM NaCl, followed by 8 column volumes of 50 mM BES pH 7.0, 500 mM NaCl) was employed for specific elution of the CD4-gamma2 chimeric heavy chain homodimer. The CD4-gamma2 chimeric heavy chain homodimer was eluted from the column in 50 mM BES pH 7.0, 500 mM NaCl. The peak fractions were then pooled and concentrated to yield a final protein concentration of at least 1 mg/ml. The pooled and concentrated fractions were then applied to a 120 ml column of Sephacryl S-300HR previously equilibrated with PBS, at a flow rate of 8 ml/hr. The CD4-gamma2 chimeric heavy chain homodimer fraction was specifically eluted in PBS, and concentrated to at least 1 mg/ml.

5. Demonstration of binding of CD4-gamma2 chimeric heavy chain homodimer to the HIV envelope glycoprotein gp120:

CosM5 transfectants expressing CD4-gamma2 chimeric heavy chain homodimer were incubated for 72 hours in DMEM containing 10% IgG-free fetal calf serum. Unlabeled medium was then collected and used to precipitate $^{35}$S-methionine-radiolabelled HIV gp120. After incubation of CD4-gamma2 chimeric heavy chain homodimer containing medium containing $^{35}$S-methionine-labelled gp120, the complexes were adsorbed to Protein A-sepharose. Protein A-sepharose complexes were recovered by centrifugation, and the precipitates were analyzed by SDS-PAGE under reducing conditions followed by fluorography (FIG. 7). Alternatively, aliquots of purified CD4-gamma2 chimeric heavy chain homodimer from CHO cells were also used to precipitate $^{35}$-S-radiolabelled gp120 using the same procedure.

6. Determination of plasma half-life and placental transfer of CD4-gamma2 chimeric heavy chain homodimer:

Determination of the plasma half-life and placental transfer are performed by well established techniques. Briefly, rabbits or monkeys are injected intravenously or instramuscularly with purified CD4-gamma2 chimeric heavy chain homodimer. At various time points post-injection, plasma samples are taken, and the quantity of the CD4-gamma2 chimeric heavy chain homodimer present in the serum is measured by ELISA. In addition, pregnant monkeys are also injected either IV or IM with CD4-gamma2 chimeric heavy chain homodimer and the concentration determined in the cord blood and the serum of the newborn monkey. Determination and comparison of the quantity of the CD4-gamma2 chimeric heavy chain homodimer in the mother's serum as well as in the cord blood and serum of the newborn indicates the relative rate of transport across the placenta of these molecules.

7. Determination of FcR binding and macrophage infectivity of CD4-gamma2 chimeric heavy chain homodimer.

Determination of FcR binding and microphage infectivity of CD4-gamma2 chimeric heavy chain homodimer are performed by well established techniques. For these studies, U937 cells (a human monocytic cell line expressing FcR1 and FcRII), purified monocyte/macrophage populations from human peripheral blood, and Hela cells constitutively expressing recombinant human FcRs are utilized. In addition, monoclonal antibodies specific for FcR1 and FcRII are commercially available. Briefly, radiolabelled monomeric or aggregated CD4-gamma2 chimeric heavy chain homodimer is incubated with the above cells and appropriate control cells at 4 degrees Celsius over various time points. At the end of each incubation, the cells are solubized and the cell-associated radioactivity is determined to establish the amount of CD4-gamma2 chimeric heavy chain homodimer specifically bound to each cell type. As controls, radiolabelled normal monomeric or aggregated human IgG2 are used to determine the levels of specific antibody binding. Furthermore, competing the radiolabelled component with unlabelled monomeric or aggregated normal human IgG2, or monoclonal antibodies to FcRI or FcRII, will establish the binding efficiency and specificity of CD4-gamma2 chimeric heavy chain homodimer to each cell type.

To ascertain whether the CD4-gamma2 chimeric heavy chain homodimer mediates enhancement of HIV infection of monocytes/macrophages, HIV-1 is incubated with media alone or either monomeric or aggregated CD4-gamma2 chimeric heavy chain homodimer at several dilutions. As controls, sera from normal individuals and HIV-infected individuals are used (31). After incubation for one hour at 4 degrees Celsius, the 'opsonized' virus is added to the cell types described in the paragraph above. At various time points after infection, the media is harvested and assayed for viral reverse transcriptase activity to determine the degree of viral infection. As controls, sCD4, OKT4a or Leu3a are included during the infection of the cells. In addition, various dilutions of the CD4-gamma2 chimeric heavy chain homodimer and appropriate controls are first incubated with the cells at 4 degrees Celsius to allow binding. HIV is then added and infecting assayed by viral reverse transcriptase activity.

8. HIV binding assay:

Binding of HIV was performed as previously described (43, 44). Briefly, concentrated HIV-1 preparations were incubated with various dilutions of sCD4, CD4-gamma2, or CD4-gamma2, for 30 minutes and then added to $5\times10^5$ CEM cells. Bound virus was detected by indirect immunofluorescence and cytofluorography as previously described (44).

9. Neutralization assay:

The microculture assay for productive viral replication was as previously described (43, 45). Briefly, dilutions of sCD4, CD4-gamma2, or CD4-gamma2 were incubated for 30 minutes with 100 $TCID_{50}$ HIV-1 at room temperature. The mixtures were added to PHA-stimulated lymphocytes and incubated at 37° C. overnight. The cells were then washed and plated in microculture at $1\times10^5$ cells/culture; and 10 cultures per dilution were monitored for reproductive viral replication by detection of HIV antigen in culture supernates 8 and 12 days later.

B. Construction of CD4-IgG2 Chimeric Heavy Chain and CD4-kappa Chimeric Light Chain for Expression of CD4-IgG2 Chimeric Heterotetramer 1. Introduction This invention describes a CD4-gamma2 chimeric heavy gene encoding a CD4-gamma2 chimeric heavy chain homodimer which is effectively secreted from transformed mammalian cells. This chimeric molecule was designed to contain sequences from the human IgG2 heavy chain which allow for efficient homodimer assembly and secretion. The CH1 region of the IgG heavy chains is responsible for retaining heavy chain molecules itracellularly and for formation of heterotetramers with light chains (24). In order to efficiently produce CD4-gamma2 chimeric heavy chain homodimers, the CD4-gamma2 chimeric heavy chain gene described above specifically lacks the CH1 domain. The resulting homodimer contains two CD4 and V1V2 moieties and therefore has the potential of being bivalent with respect to gp120 binding and having enhanced avidity for HIV compared to sCD4.

In addition, this invention describes the construction of CD4-IgG2 chimeric heterotetramers which contain two heavy chains and two light chains. The resulting heterotetramer, containing two or four CD4 V1V2 moieties, and has the potential of being tetravalent with respect to gp120 binding and having enhanced avidity for HIV compared to sCD4. The CD4-IgG2 chimeric heavy chain gene used to produce CD4-IgG2 chimeric heterotetramer contains the entire heavy chain constant region, including the CH1 domain. The inclusion of the CH1 domain facilitates efficient intracellular association with light chains, affording the potential for secreted, disulfide-bonded heterotetramers. Both the CD4-IgG2 chimeric heavy chain gene and the CD4-kappa chimeric light chain gene contain the C1C2 domains of CD4. Efforts to express CD4-IgG2 chimeric heavy chains or CD4-kappa chimeric light chains (either alone or in combination) containing only the V1 domain of CD4 were unsuccessful.

2. Construction of CD4-IgG2 chimeric heavy expression vector and CD4-kappa chimeric light chain expression vector for production of CD4-IgG2 chimeric heterotetramers.

a. Construction of CD4-IgG2 Chimeric Heavy Chain Mammalian Expression Vector

The human CD4 cDNA sequence is excised from the plasmid pSP6T4 (4) as an EcoR1/Stu1 restriction fragment. The 0/70 kilobase fragment is isolated and cloned into Ecro1/Sma1-digested M13m18. The resulting vector (M13mp18 (CD4)) is then isolated and digested with BamH1. The BamH1 sites of the M13mp18 (CD4) are made flush ended with the Klenow fragment of DNA polymerase 1. After heat inactivation of the polymerase for 15 minutes at 65 degrees Celsius, the linearized M13mp18 (CD4) vector is then digested with Pst1 and purified.

In order to excise a fragment containing the CH1 exon of the human gamma2 heavy chain gene, the plasmid pBr gamma2 (36) is digested with SacII, and the SacII sites are then made flush using T4 DNA polymerase. After heat inactivation of the polymerase, the fragment is then digested with Pst1. The resulting SacII (flush-Pst1 fragment containing the CH1 exon is then purified and ligated to the M13mp18 (CD4) vector described in the above paragraph. After transformation of competent TV1 cells, the resulting recombinants are screened by restriction analysis for the presence of both CD4 and CH1 sequences which contain in tandem CD4 (EcoR1/Stu1—CH1 (SacII (flush)/pst1). Oligonucleotide-mediated site-directed mutangenesis is then performed to juxtapose the CD4 and CH1 sequences in frame. The resulting chimeric DNA molecule contains the V1V2 domains of CD4 fused to the CH1 domain of gamma2 heavy chain. Mutangenesis is performed on single-stranded DNA isolated from recombinant phage from transformed TG1 cells (Amersham). Template DNA is annealed with a 33-mer oligonucleotide (5'-GGGCCCTTGGTGGA GGCGAAAGCTAGCACCACG-3', SEQ. ID. NO. 9) containing sequences which join the last codon encoding Phe (179) from V1V2 of CD4 to the first codon of the CH1 domain for gamma2 heavy chain (encoding Ala). After second strand synthesis, double stranded DNA is transformed into competent TG1 cells. Isolated plaques are then grown in fresh TG1 cells and single-stranded DNA is purified for DNA sequencing. All mutations are confirmed by dideoxy sequencing using the Sequenase system (USB). Plaques containing the chimeric genes with the correct sequence as determined by restriction analysis are then grown in TG1 cells, and the Rf DNA is isolated from the cells.

Rf DNA from the CD4-CH1 chimeric gene is then linearized by digestion with Pst1. The Pst1 linearized vector is then BAP treated and ligated to the Pst1—Pst1 DNA fragment of the plasmid pBr gamma2 containing the hinge, CH2, and CH3 exons of the human gamma2 heavy chain gene. The correct orientation of the Pst1—Pst1 fragment with respect to the chimeric CD4-CH1 fragment is then verified by restriction analysis. The resulting chimeric gene encodes a protein containing the V1V2 domains of the CD4 followed by the CH1, hinge, CH2, and CH3 regions of gamma2 heavy chain (FIGS. 2A, 2B, and 4).

The CD4-IgG2 chimeric heavy chain DNA molecule is isolated from the recombinant Rf DNA following Rf linearization with EcoR1. The EcoR1 sites in the linearized DNA are filled in with the Klenow fragment of DNA polymerase I. The flush ended DNA is then ligated overnight at 15 degrees Celsius with T4 DNA ligase to a 100-fold molar excess of HindIII linkers. After heat inactivation of T4 DNA ligase for 15 minutes at 70 degrees Celsius, the HindIII-linkered DNA is extensively digested with HindIII to liberate a fragment containing the CD4-IgG2 chimeric heavy chain gene. This HindIII fragment is then purified and ligated to the expression vector pcDNA-1 (Invitrogen), which was previously digested with HindIII and BAP treated. The resulting plasmid is then transformed into MC1061/ P3 cells. Plasmid DNA is isolated form recombinant clones, and verification of the presence of the HindIII insert and orientation of the insert with respect to the cytomegalovirus (CVHV) promoter in the plasmid is made by restriction analysis. The resulting mammalian expression plasmid which encodes a CD4-IgG2 chimeric heavy chain is designated CD4-IgG2HC-pRcCMV.

b. Construction of a CD4-kappa Chimeric Light Chain Mammalian Expression Vector

The human kappa light chain constant region is excised from the plasmid pCNkappa light as an MseI fragment. The purified MseI fragment is then made flush ended using the Klenow fragment of DNA polymerase 1. M13mp18 Rf is then linearized with HindIII, and the flush ended MseI kappa light chain fragment is ligated to M13mp18 at the flush ended HincIII site in the vector. After transformation of TG1 cells, the recombinants are confirmed for the presence of the insert and the correct orientation within the vector by restriction analysis. Rf is purified from infected TG1 cells and digested with EcoR1 and Sma1. The purified vector containing the kappa light chain constant region is then ligated to the EcoR1/Stu1 fragment of the human CD4 cDNA described above. The resulting recombinants are then verified for the presence and orientation of both inserts containing in tandem CD4 (EcoR1/Stu1)—Ckappa (MseI (flush)/MseI (flush)), and single-stranded DNA is purified for oligonucleotide-mediated site directed mutangenesis. Template DNA is annealed to a 33-mer oligonucleotide (5'-GATGGRGCAGCCACAGRGAAAGCRAGCAGGACG-3', SEQ. ID. NO. 10) containing sequences which join the last codon encoding Phe (179) from V1V2 of CD4 to the first codon of the kappa light chain constant domain (encoding thr). After second strand synthesis, double-stranded DNA is transformed into competent TG1 cells, and isolated plaques are grown in fresh TG1 cells for DNA sequencing. The presence of the mutation is confirmed by dideoxy sequencing. Plaques containing chimeric genes with the correct sequence are then grown in TG1 cells, and if Rf DNA is isolated from the cells. The resulting DNA molecule encodes a protein containing the V1V2 domains of CD4 followed by the constant region of kappa light chains (FIGS. 2A, 2B and 5).

The CD4-kapa chimeric light chain DNA molecule is isolated from the recombinant Rf DNA following Rf linearization with EcoR1. The EcoR1 sites in the linearized DNA are filled in with the Klenow fragment of DNA polymerase I. The flush ended DNA is then ligated overnight at 15 degrees Celsius with T4 DNA ligase to a 100-fold molar excess of HindIII linkers. After heat inactivation of T4 DNA ligase for 15 minutes at 70 degrees Celsius, the HindIII linkered DNA is extensively digested with HindIII to liberate a fragment containing the CD4-kappa chimeric light chain gene. This HindIII fragment is then purified and ligated to the expression vector pcDNA-1 (Invitrogen), which was previously digested with HindIII and BAP treated. THe resulting plasmid is then transformed into MC1061/P3 cells. Plasmid DNA is isolated from recombinant clones, and verification of the presence of the HindIII insert and orientation of the insert with respect to the cytomegalovirus (CMV) promoter in the plasmid is made by restriction enzyme analysis. The resulting mammalian expression plasmid which encodes a CD4-kappa chimeric light chain is designated CD4-kLC-pRcCMV.

3. Co-expression of CD4-IgG2HC-pRcCMV and CD4-kLC-pRcCMV in Mammalian Cells to Produce CD4-IgG2 Chimeric Heterotetramer a. Transient Expression CosM5 cells grown in DMEM containing 10% fetal calf serum are split to 75% confluence. On the following day, the cells were transfected for 16–20 hours with 5 micrograms of CsCl purified CD4-IgG2HC-pRcCMV DNA and 5 micrograms of CsCl purified CD4-kLC-pRcCMV plasmid DNA by the standard CaPO (4)precipitation technique. After transfection, fresh medium is added to the cells. Analysis of the products synthesized 48–72 hours post-transfection is performed by radiolabelling of transfectants with $^{35}$S-methionine for 12–18 hours followed by precipitation of media and cell lysates using anti-CD4 antibodies or by incubation with Protein A-sepharose beads alone or followed by SDS-PAGE under reducing or non-reducing conditions. In addition, analysis of media and cell lysates is performed 48–72 hours post-transfection by standard Western blotting procedures.

b. Stable Expression

Dhfr-Chinese hamster ovary cells (CHO) are transfected with 20 micrograms of CsCl purified DNA in a ratio of 1000:10000:1 CD4-IgG2HC-pRcCMV:CD4-kLC-pRcCMS:p410 (p410 is an expression plasmid containing the dhfr gene), although other ratios may also be used. At approximately 3–5 days post-transfection, cells are placed in selective medium (nucleoside-free alpha MEM containing 10% dialyzed fetal calf serum). At approximately 10–15 days post-selection, individual cell clones are picked. The clones are then analyzed for stable expression of CD4-IgG2 chimeric heterotetramers by several screening techniques, such as ELISA and precipitation with Protein A-sepharose beads followed by SDS-PAGE under reducing or non-reducing conditions. Clones expressing the highest levels are subjected to successive rounds of amplification of the newly introduced DNA sequences in increasing concentrations of methotrexate. Stable CHO cell lines are thus generated which secrete high levels of CD4-IgG2 chimeric heterotetramer.

4. Purification of CD4-IgG2 chimeric heterotetramers from CHO conditioned media:

CD4-IgG2 chimeric heterotetramers are purified using Protein A-Sepharose column chromatography, CHO cells secreting CD4-IgG2 chimeric heterotetramers are grown to high density in roller bottles in medium containing alpha MEM with 10% IgG-free fetal calf serum. Conditioned media is collected, clarified by centrifugation, and diluted 1:1 with PBS with/or without detergent (i.e. Tween) in this and subsequent buffers. The diluted media is then applied to a 5 ml column of Protein A-Sepharose fast flow previously equilibrated with PBS, at a flow rate of 60 ml/hour. After extensive washing, the bound material is eluted with 100 mM glycine/HCl, pH 3.5, directly onto an aliquot of 1 M Tris, HCl pH 8.0 to immediately neutralize the eluted fractions. Fractions are then analyzed by SDS-PAGE under reducing and non-reducing conditions followed by silver staining and pooled (FIG. 8).

5. Demonstration of binding of CD4-IgG2 chimeric heterotetramer to the envelope glycoprotein gp120:

CosM5 transfectants expressing CD4-IgG2 chimeric heterotetramers are incubated for 72 hours in DMEM containing 10% IgG-free fetal calf serum. Unlabelled medium in then collected and used to precipitate $^{35}$S-methionine-radiolabelled HIV gp120. After incubation of CD4-IgG2 chimeric heterotetramer containing medium with $^{35}$S-methionine-labelled gp120, the complexes are adsorbed to Protein A-sepharose. Protein A-Sepharose complexes are recovered by centrifugation, and the precipitates are analyzed by SDS-PAGE followed by fluorography. Alternatively, aliquots of purified CD4-IgG2 chimeric heterotetramers from CHO cells are also used to precipitate $^{35}$S-radiolabelled gp120 using the same procedure.

6. Determination of plasma half-life and placental transfer of CD4-IgG2 chimeric heterotetramer:

Determination of the plasma half-life and placental transfer are performed by well established techniques. Briefly, rabbits or monkeys are injected intravenously or instramuscularly with purified CD4-IgG2 chimeric heterotetramer. At various time points post-injection, plasma samples are taken, and the quantity of the CD4-IgG2 chimeric heterotetramer present in the serum is measured by ELISA. In addition, pregnant monkeys are also injected either IV or IM with CD4-IgG2 chimeric heterotetramer and the concentration determined in the cord blood and the serum of the newborn monkey. Determination and comparison of the quantity of the CD4-IgG2 chimeric heterotetramer in the mother's serum as well as in the cord blood and serum of the newborn indicates the relative rate of transport across the placenta of these molecules.

7. Determination of FcR binding and macrophage infectivity of CD4-IgG2 chimeric heterotetramer:

Determination of FcR binding and macrophage infectivity of CD4-IgG2 chimeric heterotetramer are performed by well established techniques. For these studies, I937 cells (a human monocyte cell line expressing FcR1 and FcRII), purified monocyte/macrophage populations from human peripheral blood, and Hela cells constitutively expressing recombinant human fcRs are utilized. In addition, monoclonal antibodies specific for FcR1 and FcRII are commercially available. Briefly, radiolabelled monomeric or aggregated CD4-IgG2 chimeric heterotetramer is incubated with the above cells and appropriate control cells at 4 degrees Celsius over various time points. At the end of each incubation, the cells are solubized and the cell-associated radioactivity is determined to establish the amount of CD4-IgG2 chimeric heterotetramer specifically bound to each cell type. As controls, radiolabelled normal monomeric or aggregated human IgG2 are used to determine the levels of specific antibody binding. Furthermore, competition of the radiolabelled component with unlabelled monomeric or aggregated normal human IgG2, or monoclonal antibodies to FcRI or FcRII, will establish the binding efficiency and specificity of CD4-IgG2 chimeric heterotetramer to each cell type.

To ascertain whether the CD4-IgG2 chimeric heterotetramer mediates enhancement of HIV infection of monocytes/macrophages, HIV-1 is incubated with media alone or either monomeric or aggregated CD4-IgG2 chimeric heterotetramer at several dilutions. As controls, sera from normal individuals and HIV-infected individuals are used (31). After incubation for one hour at 4 degrees Celsius, the 'opsonized' virus is added to the cell types described in the paragraph above. At various time points after infection, the media is harvested and assayed for viral reverse transcriptase activity to determine the degree of viral infection. As controls, sCD4, OKT4a or Leu3a are included during the infection of the cells. In addition, various dilutions of the CD4-IgG2 chimeric heterotetramer and appropriate controls are incubated first with the cells at 4 degrees Celsius to allow binding. HIV is then added and infection assayed by viral reverse transcriptase activity.

B. Results

A CD4-gamma2 chimeric heavy chain gene encoding a CD4-gamma2 chimeric heavy chain homodimer was generated by ligating the leader-V1–V2 segment of the human CD4 cDNA (4) to the hinge exon of the human gamma2 heavy chain gene (30) (FIG. 1A). The resulting recombinant DNA molecule (designated CD4-IgG2-Rf) encodes the signal sequence and two amino-terminal immunoglobulin-like domains of the CD4 protein (the first 179 amino acids of mature CD4) followed by the hinge (15 amino acids), CH2 (110 amino acids), and CH3 (107 amino acids) regions of the gamma2 heavy chain protein (FIG. 3). This recombinant DNA molecule also contains two introns present within the gamma2 heavy chain gene: between the H and CH2 domains, and between the CH2 and CH3 domains. This CD4-gamma2 chimeric gene was designed to encode a CD4-gamma2 chimeric heavy chain homodimer which specifically lacks the CH1 domain of the gamma2 heavy chain. Expression of the CH1 domain without accompanying light chains prevents efficient heavy chain secretion from mammalian cells (25).

Figure 1B:
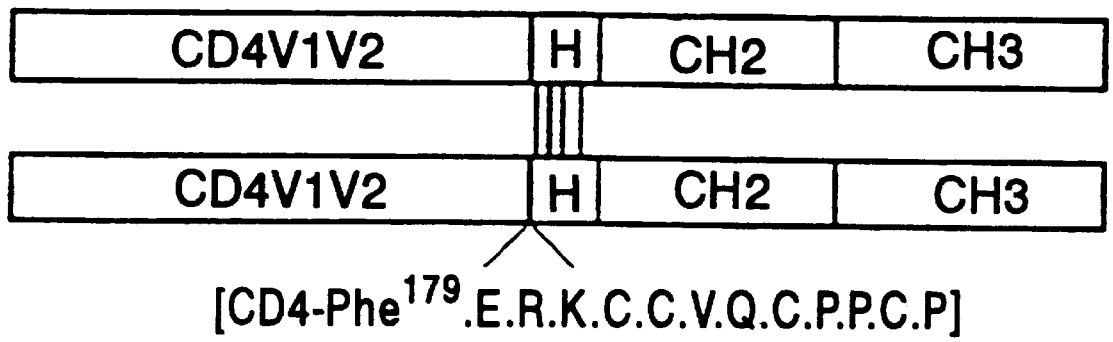

In the CD4-gamma2 chimeric heavy chain homodimer, the hinge region of one chain contains four cysteine residues, affording the potential of four interchain disulfide bonds (FIG. 1B). Similarly, naturally-occurring human IgG2 contains four interchain disulphide bonds between the gamma2 heavy chains.

The CD4-gamma2 chimeric heavy chain gene was subcloned into the mammalian expression vection pcDNA1. This vector contains the following DNA elements: the cytomegalovirus (CMV) immediate early promoter and enhancer driving transcription of the CD4-gamma2 chimeric heavy chain gene; an SV40 polyadenylation sequence; and an SV40 origin of replication which allows replication of the plasmid to high copy number in CosM5 cells. The resulting CD4-gamma2 heavy chain mammalian expression vector (designated CD4-IgG2-pcDNA1) was transfected into CosM5 cells which were then radiolabelled with $^{35}$S-methionine 48–72 hours post-transfection. The radiolabelled medium was analyzed by precipitation with Protein A-sepharose beads and SDS-PAGE followed by fluorography (FIG. 6). Under reducing conditions, a protein migrating at a relative molecular mass (Mr) of approximately 47 kilodaltons is precipitated. When the precipitated material was run on SDS-PAGE under nonreducing conditions, a protein migrating at an Mr of approximately 94 kilodaltons is observed, indicating that the CD4-gamma2 chimeric heavy chains assemble and are secreted as homodimers. In addition, these results demonstrate that the secreted CD4-gamma2 chimeric heavy chain homodimers contain in intact immunoglobulin Fc domain since they bind Protein A. Further characterization by Western blot analysis of the proteins secreted into the medium 48–72 hours post-transfection was performed using a rabbit polyclonal antiserum raised against purified soluble human CD4. Similar to the results obtained by precipitation, when the medium was run on SDS-PAGE under reducing conditions, followed by Western transfer to nitrocellulose, the major immunoreactive protein migrates at an Mr of approximately 47 kilodaltons. Under nonreducing conditions, the major immunoreactive protein migrates at an Mr of approximately 94 kilodaltons. Taken together, these results demonstrate that the CD4-gamma2 chimeric heavy chain is produced and secreted as a homodimer of the predicted molecular weight.

The above results demonstrate that the Fc portion of CD4-gamma2 chimeric heavy chain homodimer, encoded by the constant regions of the gamma2 heavy chain gene, binds Protein A and is therefore functionally active. In order to determine if the CD4 portion is functionally intact, CD4-gamma2 chimeric heavy chain homodimers were assayed for their ability to bind to the HIV exterior envelope glycoprotein, gp120 (FIG. 7). Unlabelled medium from CosM5 cells transfected with CD4-IgG2-pcDNA1 DNA was incubated with $^{35}$S-methionine-labelled gp120. CD4-gamma2 chimeric heavy chain homodimer/gp120 complexes were precipitated by incubation with Protein A-sepharose beads, and the precipitates were analyzed by SDS-PAGE under reducing conditions followed by fluorography. These results demonstrate that the CD4-gamma2 chimeric heavy chain homodimer efficiently recognizes HIV gp120 and binds with high affinity. These observations, taken together with the results described in the above paragraph, demonstrate that CD4-gamma2 chimeric heavy chain homodimer contains functionally active regions of both CD4 and gamma2 heavy chain.

In order to stably produce large quantities of the CD4-gamma2 chimeric heavy chain homodimers, the CD4-IgG2-pcDNA1 vector was cotransfected with the plasmid p410 (encoding the enzyme dihydrofolate reductase (dhfr)) into dhfr-Chinese Hamster Ovary (CHO) cells. Approximately two weeks post-transfection, individual clones growing in nucleoside free alpha MEM and 10% dialyzed fetal calf serum (and therefore dhfr+) were isolated and analyzed for co-expression of CD4-gamma2 chimeric heavy chain homodimers by precipitation and ELISA. The highest producing cell lines were identified and subjected to stepwise increasing concentrations of methotrexate which selects for amplification of the newly introduced DNA sequences. A CHO cell line expressing 10 micrograms/milliliter of CD4-gamma2 chimeric heavy chain homodimer was used for stable, constitutive production in roller bottles. The cells were grown to confluence in alpha MEM containing 10% IgG-free fetal calf serum. The cells were then fed every other day and two day old conditioned medium was used for purification of the CD4-gamma2 chimeric heavy chain homodimer. Conditioned medium was diluted 1:1 with phosphate-buffered saline (PBS) and applied to a 5 ml column a Protein A-sepharose fast flow (Pharmacia) at a flow rate of 60 milliliters/hour. The column was then washed with 10 column volumes of PBS and the bound material was eluted with 100 mM glycine pH 3.5. The eluted material was collected directly into 50 µl of 1 M Tris. HCl pH 8.0 to neutralize the eluant. Fractions having an OD(280) of greater than 0.1 were analyzed by SDS-PAGE followed by silver staining or Western blot analysis, and the peak fractions were pooled. A single band was specifically eluted from the Protein A-sepharose column with an Mr corresponding to the CD4-gamma2 chimeric heavy chain homodimer (FIG. 8). Western blot analysis confirms that the eluted protein is immunoreactive with polyclonal antiserum raised against soluble human CD4. In addition, the purified protein retains the ability to bind with high affinity to $^{35}$S-methionine-labelled gp120. These results demonstrate the stable, high-level production of CD4-gamma2 chimeric heavy chain homodimers in mammalian cells, and the purification of CD4-gamma2 chimeric heavy chain homodimer which retains biological function.

The partially purified CD4-gamma2 heavy chain homodimer purified as described in FIG. 8 was effective at preventing HIV binding to CD4 cells (FIG. 9) and neutralization of infectivity of a fixed HIV inoculum (FIG. 10). In this later assay, approximately 10–25 µg/ml of CD4-gamma2 as well as sCD4 were required to prevent 50% of the cultures from becoming infected by HIV.

Further purification of CD4-gamma2 heavy chain homodimer was achieved using ion-exchange chromatography. The peak fraction from the protein A-sepharose column was applied to a 10 ml S-sepharose fast flow column preequilibrated with 50 mM BES pH 7.0, at a flow rate of 120 ml/hr. After application of the sample, the column was extensively washed with 50 mM BES pH 7.0 with increasing salt concentration (see materials and methods). CD4-gamma2 heavy chain homodimer was specifically eluted from the column in 50 mM BES pH 7.0 containing 500 mM NaCl. Following the ion exchange chromatopgraphy, we unexpectedly found the peak fractions containing the CD4-gamma2 chimeric heavy chain homodimer was still impure. Therefore, the peak fractions from the S-sepharose column were pooled, concentrated and applied to a 120 ml Sephacryl S-300HR column prequilibrated with PBS and run at a flow rate of 8 ml per hour. The peak fractions of purified CD4-gamma2 heavy chain homodimer were analyzed by SDS-PAGE and silver staining under non-reducing conditions, and the purified fractions were pooled and analyzed by SDS-PAGE followed by silver staining under non-reducing conditions (FIG. 11, lane 1), or reducing conditions (FIG. 11, lane 2). When the purified CD4-gamma2 chimeric heavy chain homodimer was run on SDS-PAGE under reducing conditions, a doublet was observed which appeared to be due to differences in glycosylation of the CD4-gamma2 chimeric heavy chain homodimer (data not shown).

A CD4-IgG2HC chimeric heavy chain gene encoding a CD4-IgG2 chimeric heavy chain was generated by ligating the leader-V1–V2 segment of the human CD4 cDNA to the CH1 exon of the human IgG2 heavy chain gene (FIG. 2A). In addition a CD4-kappa chimeric light chain gene encoding a CD4-kappa light chain was generated by ligating the leader-V1–V2 segment of the human CD4 cDNA to the constant domain of the kappa light chain gene (FIG. 2A). These CD4-IgG2 chimeric heavy chain genes and CD4-kappa chimeric light chain genes were designed to encode a CD4-IgG2 chimeric heterotetramer, in which the CD4-IgG2 heavy chain contains a CH1 domain for efficient association with kappa light chains.

Figure 12A:
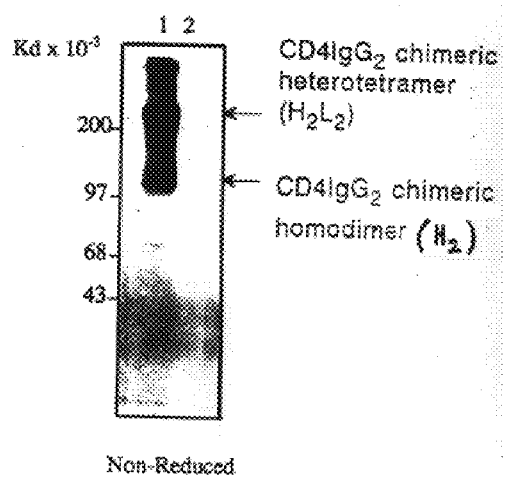
Figure 12B:
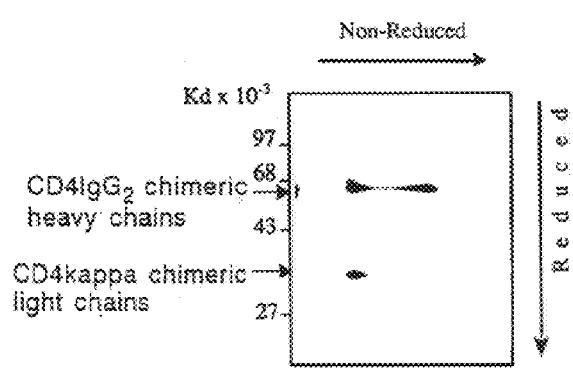

Both the CD4-IgG2 chimeric heavy chain and the CD4-kappa chimeric light chain genes were subcloned into the mammalian expression vectors pRcCMV or pPPI-2. Both vectors contain the cytomegalovirus immediate early promoter and enhancer driving transcription of the chimeric genes. In the vector pRcCMV, a second transcriptional cassette which contains the RSV promoter and enhancer is used to direct the transcription of the neomycin resistance gene. In pPPI-2, a second transcriptional cassette which contains the β-globin promoter directs the transcription of the dhfr gene (see supra). In order to stably produce large quantities of the CD4-IgG2 chimeric heterotetramer, the CD4-IgG2 chimeric heavy chain expression vector and the CD4-kappa chimeric light chain expression vector were transfected simultaneously (typically the CD4-IgG4 chimeric heavy chain gene cloned in pRcCMV was used, and CD4-kappa chimeric light chain gene cloned in pPPI-2 was used in a ratio of 1:1). Approximately two weeks post-transfection, individual clones growing in nucleoside-free alpha MEM containing 1 mg/ml G418 and 10% dialyzed fetal calf serum were isolated and analyzed for co-expression of both CD4-IgG2 chimeric heavy chains and CD4-kappa chimeric light chains by immunoprecipitation and ELISA. FIG. 12 demonstrates one clone which was selected and analyzed for the expression of both CD4-IgG2 chimeric heavy chains and CD4-kappa chimeric light chains. The CHO cell line or the untransfected parental CHO cell line were radiolabelled with $^{35}$S-methionine and $^{35}$S-cysteine for 16 hours. The radiolabelled medium was analyzed by precipitation with Protein A-sepharose beads and SDS-PAGE under non-reducing conditions followed by fluorography (FIG. 12A). Under non-reducing conditions 2 proteins migrating at relative molecular masses of approximately 140 kilodaltons and 210 kilodaltons are precipitated. When the precipitated material was run on SDS-PAGE under non-reducing conditions, 2 proteins migrating at relative molecular masses of 69 kilodaltons and 35 kilodaltons were observed, which are consistent with the relative predicted molecular masses of the CD4-IgG2 chimeric heavy chains, and CD4-kappa chimeric light chains respectively (data now shown). Further characterization has shown that the protein migrating at 210 kilodaltons on SDS-PAGE under non-reducing conditions contains both CD4-IgG2 chimeric heavy chains and CD4-kappa chimeric light chains which are covalently associated, while the protein migrating at 140 kilodaltons on SDS-PAGE under non-reducing conditions contains only CD4-IgG2 chimeric heavy chains (FIG. 12B). These data are constituent with the predicted molecular weight of the 210 kilodalton protein having 2 CD4-IgG2 chimeric heavy chains and 2 CD4-kappa chimeric light chains, covalently associated to form a molecule with the structure $H_2L_2$ (H=heavy chain, L=light chain). Furthermore, the 140 kilodalton protein seen on SDS-PAGE under non-reducing conditions is consistent with the predicted molecular weight of a CD4-IgG2 chimeric homodimer having the structure $H_2$. Taken together, these results indicate that a CHO cell line which expresses both CD4-IgG2 chimeric heavy chains and CD4-kappa chimeric light chains is able to efficiently assemble and secrete CD4-IgG2 chimeric heterotetramers.

References

1. Klatzmann, D. R. et. al. (1990) Immunodeficiency Reviews 2, 43–66.

2. Lasky, L. A., et. al. (1987) Cell 50, 975–985.
3. Maddon, P. J., et. al. (1986) Cell 47, 333–348.
4. Maddon, P. J., et. al. (1985) Cell 42, 93–104.
5. Wain-Hobson, D., et. al. (1985) Cell 40, 9–17.
6. Maddon, P. J., et. al. (1987) Proc. Natl. Acad. Sci. U.S.A., 84, 9155–9159.
7. Richardson, N. E., et. al. (1988) Proc. Natl. Acad. Sci. U.S.A. 85, 6102–6106.
8. Chao, B. H., et. al. (1989) J. Biol. Chem. 264, 5812–5817.
9. Arthos, J., et. al. (1989) Cell 57, 569–481.
10. Wang, J., et al. (1990) Nature 348, 411–418.
11. Ryu, S-E., et. al. (1990) Nature 348, 419–426.
12. Maddon, P. J. et. al. (1988) PCT WO88/01304.
13. Moore, J. P., et al (1990) Science 250, 1139–1142.
14. Schooley, R. T., et. al. (1990) Ann. Internal Med. 112, 247–253.
15. Kahn, J. O., et. al. (1990) Ann. Internal Med. 112, 254–261.
16. Daar, E. S., et. al. (1990) Proc. Natl. Acad. U.S.A. 87, 6574–6578.
17. Boss, M. A., et. al. (1989) U.S. Pat. No. 4,816,397.
18. Cabilly S., et. al. (1989) U.S. Pat. No. 4,816,567.
19. Morrison, S. L. et. al. (1984) Proc. Natl. Acad. Sci. 81, 6851–6855.
20. Capon, D. J., and Gregory, T. J., (1989) PCT WO89/02922.
21. Capon, D. J., et. al. (1989) Nature 337, 525–531.
22. Byrn, R. A., et. al. (1990) Nature 344, 667–670.
23. Berger, E. A., et. al. (1990) PCT WO90/01035.
24. Seed, B., (1989) PCT WO89/06690.
25. Hendershot, L., et. al. (1987) J. Cell Biol. 104, 761–767.
26. Traunecker, A., et. al. (1989) Nature 339, 68–70.
27. Till, M., et. al. (1988) Science 242, 1166–1168.
28. Pastan, I., et. al. (1989) J. Biol. Chem. 264, 15157–15160.
29. Gartner, S., et al. (1986) Science 233, 215–219.
30. Simister, N. E., (1990) in: Fc REceptors and the Action of Antibodies, ISBN 1-55581-016-0, pp. 57–73.
31. Perno, C-F., et. al (1990), J. Exp. Med. 171, 1043–1056.
32. Porterfield, J. S., et al. (1986), Adv. Virus Res. 31, 335.
33. Kabat, E., et al. (1987) in: Sequences of Proteins of Immunological Interest, 4th Edition.
34. Underdown, B. J., in: Fc Receptors and the Action of Antibodies, ISBN 1-55581-016-0, pp. 74–93.
35. Burton, D., (1995), Molecular Immunology 22, 161–206.
36. Oi. V. T., and Morrison, S. L., (1986) Biotechnology 4, 214–223.
37. Okayama, H., Mol. Cel. Biol., 3:280 (1983).
38. Remington's Pharmaceutical Science, 16th Ed., Mack Eds., 1980.
39. Duncan et al., Analy. Biochem. 132:68–73 (1983).
40. Thorpe et al., Cancer Res. 47:5924 (1987).
41. Ghotie et al., Cancer Res. 48:2610 (1988).
42. Maniatis, T., et. al., Molecular Cloning, Vol. 1–3, (1990).
43. Kennedy, M. S., et al. (1991) AIDS Res. and Human Retroviruses 7, 975–981.
44. McDougal, J. S., et al. (1986) J. Immunol 137, 2937–2944.
45. McDougal, J. S., et al. (1985) J. Immunol Methods 76, 171–183.

Second Series of Experiments

1. In vitro experiments

The bioactivity of CD4-IgG2 has been examined by three distinct approaches:

a) binding affinity for monomeric gp120 from a laboratory-adapted strain and a primary isolate of HIV-1.

b) inhibition of HIV-1 envelope-mediated syncytium formation using a virus-free syncytium assay.

c) neutralization studies using laboratory-adapted strains and primary isolates of HIV-1, including virus in undiluted viremic plasma from HIV-1 infected individuals.

a) Binding of CD4-IgG2 to HIV-1 gp120:

A modified ELISHA method was used to determine 50% maximal binding ($EC_{50}$) of CD4-IgG2 to HIV-1 gp120 derived from the laboratory-adapted strain HIV-$1_{LAI}$ and the primary isolate HIV-$1_{JR-FL}$. sCD4 was used as a control in these experiments. The $EC_{50}$ value is a reasonable approximation of the dissociation constant (Kd). The method was similar to that described elsewhere. Briefly, recombinant gp120 from HIV-$1_{LAI}$ of HIV-$1_{JR-FL}$ was expressed in CHO cells and purified at Progenics. The gp120 was captured onto a ELISHA plate and a range of concentrations of purified sCD4 (Progenics) or CD4-IgG2 were added. Following a 1 hour incubation at 37° C., the amount of bound protein was measured by immunosassay, and the concentration of sCD4 or CD4-IgG2 giving 50% of maximal binding ($EC_{50}$) was determined. The results are shown in Table 1:

TABLE 1

Comparison of sCD4 and CD4-IgG2 binding to HIV-1 gp120 from the laboratory-adapted strain HIV-$1_{LAI}$ and the primary isolate HIV-$1_{JR-FL}$.

| Molecule | (nM) HIV-$1_{LAI}$ | $EC_{50}$ HIV-$1_{JR-FL}$ |
|---|---|---|
| sCD4 | 1.93 | 2.22 |
| CD4-IgG2 | 1.25 | 0.64 |

These results demonstrate that CD4-IgG2 binds with nanomlar affinity to recombinant HIV-1 gp120 derived from both a laboratory-adapted strain (HIV-$1_{LAI}$) and a primary isolate (HIV-$1_{JR-FL}$). In addition, the affinity of CD4-IgG2 for immobilized recombinant gp120 is greater than that of sCD4. We have also demonstrated that CD4-IgG2 binds gp120 from 16 primary HIV-1 isolates from several different genetic clades.

b) Syncytium inhibition assay:

The anti-viral properties of CD4-IgG2 were determined using a syncytium inhibition assay which is a measure of potency in blocking cell-to-cell virus transmission. The syncytium inhibition assay was developed at Progenics and analyzes blocking of fusion between cells stably expressing HIV-$1_{IIIB}$ gp120/gp41 and cells stably expressing human CD4. Inhibition of cell fusion was compared using tetrameric CD4-IgG2, dimeric CD4-gamma2 (Progenics) and monomeric soluble CD4. Briefly, serial dilutions of each protein were added to cultures of CHO cells which stably express HIV-$1_{IIIB}$ gp120/gp41. Following a two hr incubation, C8166 (human T lymphocyte) cells were added. Syncytia were counted 48 hrs later, and the concentration of each molecule giving 50% inhibition ($IC_{50}$) determined. The results are shown in Table 2.

TABLE 2

Comparative analysis of syncytium inhibition by monomeric sCD4, dimeric CD4-gamma2 and tetrameric CD4-IgG2.

| Molecule | ($\mu$g/ml) | $IC_{50}$ nM | Relative Potency mass | molarity |
|---|---|---|---|---|
| sCD4 | 9.19 | 200 | 1.0 | 1.0 |
| CD4-gamma2 | 4.03 | 40 | 2.3 | 5.0 |
| CD4-IgG2 | 1.81 | 9 | 5.1 | 22.2 |

Potency relative to that of sCD4 is shown.

These data demonstrate that CD4-IgG2 is biologically active and inhibits syncytium formation more effectively than CD4-gamma2 or sCD4 on the basis of mass or molarity. This most likely results from the differences in the number of CD4 moieties in each molecule and the resulting variations in binding avidity for membrane-associated gp120/gp41. These results strongly suggest that CD4-IgG2 is properly folded and that all the CD4 moieties in this molecule specifically interact with the HIV-1 envelope glycoprotein.

c) In vitro neutralization assays:
 i) Neutralization of a panel of laboratory-adapted strains and primary isolates of HIV-1:

Initially, the ability of CD4-IgG2 to neutralized a panel of HIV-1 isolates in vitro using human PBMC was determined. The panel comprised two laboratory-adapted stains (HIV-$1_{LAI}$ and HIV-$1_{MN}$) and five primary HIV-1 isolates. The primary isolates, which were passaged only in human PBMC, included: the molecularly cloned viruses HIV-$1_{JR-CSF}$ and HIV-$1_{JR-FL}$ from the cerebrospinal fluid and frontal lobe, respectively, of an AIDS patient; HIV-$1_{AD6}$ from an HIV-1 infected individual prior to seroconversion; and, HIV-$1_{5108}$ from an asymptomatic individual. At least one of these viruses (HIV-$1_{JR-FL}$) is monocytotropic. The panel also included HIV-$1_{WH91-330}$ which was chosen because it is the most resistant to neutralization by monoclonal antibodies or polyclonal sera when compared to other primary HIV-1.

Briefly, 50 $TCID_{50}$ of HIV-1 was incubated with serial 5-fold dilutions of CD4-IgG2 for 30 min at 37° C. The treated virus and untreated control preparations were added to 2×10$^6$ PHA-activated normal donor PBMC. One day later the cultures were washed, and on day 7 the cellular supernatants were assayed for p24 core antigen expression using a commercial kit (Abbott Laboratories, Abbott Park, Ill.). The percent neutralization was determined by dividing the difference in p24 antigen concentration between the treated and untreated cultures by the p24 antigen concentration in the untreated control. The results are given in Table 3.

TABLE 3

Neutralization of laboratory-adapted strains[L] and primary isolates[P] of HIV-1 by CD4-IgG2.

| HIV strain | $IC_{50}$ ($\mu$g/ml) | $IC_{90}$ ($\mu$g/ml) |
|---|---|---|
| LAI[L] | 0.1 | 0.4 |
| MN[L] | 0.3 | 1.4 |
| 5108[P] | 2.1 | 14.8 |
| JR-CSF[P] | 0.4 | 9.9 |

TABLE 3-continued

Neutralization of laboratory-adapted strains[L] and primary isolates[P] of HIV-1 by CD4-IgG2.

| HIV strain | $IC_{50}$ ($\mu$g/ml) | $IC_{90}$ ($\mu$g/ml) |
|---|---|---|
| JR-FL[P] | 3.5 | 6.4 |
| WH91-330[P] | 30.3 | ~100* |
| AD6[P] | 2.5 | 17.7 |

The concentration of CD4-IgG2 giving 50% neutralization ($IC_{50}$) or 90% neutralization ($IC_{90}$) is shown (*Replicates gave 100% or 79% inhibition at 100 $\mu$g/ml).

As demonstrated in previous studies with other CD4-based molecules, the laboratory-adapted strains were more sensitive than primary isolates to neutralization by CD4-IgG2. Nevertheless, all isolates including HIV-$1_{WH91-330}$ were neutralized by CD4-IgG2, with 6 of the 7 isolates giving $IC_{50}$ values less than 4 $\mu$g/ml (20 nM) and $IC_{90}$ values less than 18 $\mu$g/ml (90 nM). A comparative study of neutralization by sCD4, CD4-gamma2 and CD4-IgG2 was performed using an subset of the viral isolates (HIV-$1_{LAI}$, HIV-$1_{MN}$, HIV-$1_{5108}$ and HIV-$1_{JR-CSF}$). $IC_{50}$ values in $\mu$g/ml for the monomeric or dimeric CD4-based proteins (not shown) were on average 18.2-fold higher (sCD4) or 7.7-fold higher (CD4-gamma2) than those of CD4-IgG2, demonstrating that CD4-IgG2 was the most potent neutralizing agent.

ii) Neutralization of divergent primary HIV-1 isolates from different genetic clades:

Applicants then compared CD4-IgG2 and 3 monoclonal antibodies (IgG1b12, 2G12 and 2F5) for their ability to neutralize widely divergent primary isolates of HIV-1, representing different genetic clades (A through F and O) of the virus. The viruses tested include the 12 clade B viruses and 18 primary isolates from other HIV-1 clades. CD4-IgG2 neutralized all the HIV-1 strains tested, both from within clade B and from the other clades (Table 4). Of the reagents tested, CD4-IgG2 was the only one with $IC_{50}$ values for all strains less than 50 $\mu$g/ml (in most cases below 10 ug/ml). Moreover, $IC_{90}$ values for CD4-IgG2 were less than 50 $\mu$g/ml for 28 of the 30 strains tested, a larger fraction than with any of the antibodies.

TABLE 4

Neutralization of B and non-B (clades A, C, D, E, F) Primary Isolates by CD4-IgG2.

| Clade | mean ID-90 | median ID-90 | % neut. viruses |
|---|---|---|---|
| B (n = 12) | 19 | 20 | 92 |
| non-B (n = 16) | 16 | 15 | 94 |
|  | mean ID-50 | median ID-50 | % neut. viruses |
| B (n = 12) | 7.0 | 6.2 | 100 |
| non-B (n = 16) | 7.0 | 4.8 | 100 |

In summary, CD4-IgG2 neutralized these diverse HIV-1 strains more broadly and potently than any of the monoclonal antibodies tested. These results indicate that CD4-IgG2 would be valuable for use against HIV-1 strains found throughout the world.

iii) Ex Vivo neutralization of HIV-1 in the plasma of HIV-1 infected individuals:

The in vitro studies discussed above were extended by testing CD4-IgG2 for ability to neutralized viremic plasma from HIV-1 infected individuals (an ex vivo assay).

Briefly, plasma or dilutions of viremic plasma from HIV-1 infected individuals were incubated with PHA-activated normal PBMC. 25 μg CD4-IgG2 (or antibody) was added to each culture, with a final culture volume of approximately 1 ml. After 7 days, a p24 antigen assay was performed on the culture supernatant to assess the degree of HIV-1 replication.

Several broadly neutralizing human monoclonal antibodies were tested in parallel with CD4-IgG2 in these assays (all proteins at 25 μg/ml), including IgG12—a broadly neutralizing MAb directed to the CD4 binding site; 19b—a cross-reactive V3 loop MAb; A-32—a broadly neutralizing MAb directed at a discontinuous epitope of gp120 (described below); 21h—a CD4 binding site MAb. The results obtained with two patients are illustrated in FIG. 13. In this figure, a measure of the amount of infections HIV-1 in the plasma samples is given by the results in control cultures (medium alone or control IgG), where virus replication could be easily detected in cultures exposed to a 125-fold or greater dilution of plasma. CD4-IgG2 potently neutralized HIV-1 in these samples, reducing virus replication to background levels even in undiluted viremic plasma. The monoclonal antibodies tested also neutralized HIV-1, but were less effective when compared to CD4-IgG2 in undiluted viremic plasma.

Similar data were obtained using viremic plasma samples from four other donors. As shown in FIG. 14, CD4-IgG2 reduced the HIV-1 titer in the plasma samples from all six donors by between 5- and 625-fold, where the reductions in HIV-1 titers resulting from treatment of the viremic plasma with CD4-IgG2 or sCD4 are compared.

These studies demonstrate that CD4-IgG2 potently neutralizes HIV-1 present in the plasma of HIV-infected individuals. The concentrations of CD4-IgG2 required to neutralize HIV-1 in vitro or ex vivo were at levels which should be readily achieved in vivo.

2. In vivo experiments hu-PBL-SCID -mouse model:

In this model, immunodeficient mice are reconstituted with human PBLs and can then be infected by HIV-1[23]. The protective effect of antibodies or other antiviral agents can be tested in this model. hu-PBL-SCID mice have been used to show that a monoclonal antibody (BAT 123) to the V3 loop of HIV-1$_{IIIB}$ can protect in vivo against infection by the homologous virus. Protection was achieved both by dosing the animal prior to infection, but also by treating the animal with antibody up to 4 hours after exposure to HIV-1. The dose was 1 mg/kg in both cases, and resulted in a peak serum concentration of 16 μg/ml BAT 123, which is 50-fold greater than the in vitro IC$_{90}$ against HIV-1$_{IIIB}$. When a dose of 0.1 mg/kg was used, less than 50% protection was achieved against HIV-1$_{IIIB}$. No protection was seen against heterologous strains of HIV-1 using a does of 1 mg/kg BAT 123.

Protection studies using CD4-IgG2 were performed by the same method as used with BAT 123. Briefly, non-leaky phenotype mice were reconstituted by intraperitoneal injection of 20×10$^6$ freshly isolated normal human PBL. Pharmacokinetic analysis was performed by intraperitoneal injection of 3 hu-PBL-SCID mice with CD4-IgG2 at 10 mg/kg. Bleeds were performed from the tail vein of the mice before injection and a 6 hrs and 1, 3, 7 and 14 days after injection. The serum concentration of the injected CD4-IgG2 was determined of ELISHA.

For protection studies, infection of hu-PBL-SCID mice was' performed two weeks after PBL reconstitution. hu-PBL-SCID mice were injected intraperitoneally with 0.5 ml diluted cell-free stock of HIV-1$_{LAI}$, or the primary isolates HIV-1$_{JR-CSF}$ (molecular clone) and HIV-1$_{AD6}$ (acute seroconverter), containing 10 mouse infectious doses. This virus inoculum has been shown to infect at least 80% of hu-PBL-SCID mice. For protection experiments, CD4-IgG2 or control human IgG in 0.5 PBS was injected intraperitoneally 1 hr before HIV-1 inoculation. Three weeks after viral challenge the mice were killed and cells recovered from peritoneal lavage and spleens. Then 2×10$^5$ peritoneal lavage cells or 5×10$^6$ spleen cells (with 10-fold serial dilutions) were incubated with 2×10$^6$ PHA-activated PBL from HIV-1 seronegative donors in an end-point dilution culture. Co-cultures were monitored weekly for four weeks for the presence of HIV-1 p24 core antigen in the culture supernatant using a commercial ELISHA (Abbott Laboratories). Cultures were considered HIV-1 positive if a single sample contained >1000 pg/ml of if two consecutive samples contained >200 pg/ml p24 antigen. The positive well containing the fewest spleen cells was taken as the end-point and the viral titers expressed as tissue culture infectious doses (TCID) per 10$^6$ cells.

Analysis of CD4-IgG2 in the plasma of animals injected with 10 mg/kg demonstrated a mean peak serum titer of 112 μg/ml, at 6 hrs post-injection. The terminal half-life of CD4-IgG2 in the mice was approximately 1 day. Table 5 summarizes the protection data obtained when mice were treated with 10 mg/kg or 50 mg/kg CD4-IgG2 or control human IgG.

TABLE 5

Protection of hu-PBL-SCID mice from HIV-1 infection by CD4-IgG2 or control human IgG.
Number of HIV-infected mice/Total, following treatment with:

| HIV-1 Strain | CD4-IgG2 | | Control human IgG | |
|---|---|---|---|---|
| | 10 mg/kg | 50 mg/kg | 10 mg/kg | 50 mg/kg |
| LAI | 0/8 | n.d. | 5/8 | n.d. |
| JR-CSF | 2/6 | 0/5 | 5/6 | 5/5 |
| AD6 | 6/6 | 1/5 | 5/6 | 4/4 |

The HIV-1 strains tested were the laboratory-adapted strain LAI, and the primary isolates JR-CSF and AD6. Animals were dosed at 10 mg/kg or 50 mg/kg.
n.d.: not done.

CD4-IgG2 protected the hu-PBL-SCID mice from infection by all three HIV-1 strains. The three viral strains exhibited the same relative susceptibility to neutralization by CD4-IgG2 in vivo as had been found in vitro. HIV-1$_{LAI}$ was the most susceptible, with complete protection at a dose of 10 mg/kg, where the peak plasma concentration is 280× the in vitro IC$_{90}$. HIV-1$_{JR-CSF}$ was intermediate in susceptibility with 60% protection of mice at 10 mg/kg and 100% protection at 50 mg/kg, corresponding to plasma concentrations of 11× and 56× the IC$_{90}$ respectively. 80% protection of AD6-exposed mice was seen at 50 mg/kg, where the plasma concentration is 32× the IC$_{90}$.

These results clearly demonstrate that pre-treatment by CD4-IgG2 can protect against infection by primary isolates of HIV-1 in an in vivo model. Similar to the results obtained with BAT 123, it is necessary to achieve a CD4-IgG2 plasma concentration of approximately 50-fold greater than the IC$_{90}$ of each HIV strain to achieve protection against that strain in hu-PBL-SCID mice. However, in contrast to BAT 123 and other antibodies, the in vitro data with CD4-IgG2 demonstrate that this protein is capable of neutralizing a broad range of primary HIV-1 isolates. The hu-PBL-SCID mice data presented here show it is also possible to protect against diverse strains of the virus in vivo, including primary HIV-1 isolates.

3. Pharmacokinetics:

A single-dose pharmacokinetic study of CD4-IgG2 was performed in rabbits. Samples (0.2 mg) of CD4-IgG2, of sCD4 for comparative purposes, were injected into the ear veins of 5 replicate New Zealand White rabbits and blood samples collected from the opposite ear vein artery before injection and at pre-determined intervals following injection. The concentrations of the molecules in plasma were determined by ELISHA. α and β plasma half-lives were calculated using a two compartment model (PCNONLIN version 4; SCI Software, Lexington, Ky.). The calculated α and β plasma half-lives are shown in Table 6, in comparison with sCD4.

TABLE 6

Pharmacokinetics of sCD4 and CD4-IgG2 in rabbits.

| Molecule | α half-life | β half-life |
| --- | --- | --- |
| sCD4 | 7.6 minutes | 16.8 minutes |
| CD4-IgG2 | 1.3 hours | 26.4 hours |

These results demonstrate that CD4-IgG2 has a β or terminal half-life about 100-fold greater than that of sCD4, presumably resulting from the larger mass of CD4-IgG2 and presence of an Fc moiety in this protein. The terminal half-life of CD4-IgG2 is important in determining the dose level and frequency of administration which would be required to achieve a protective or therapeutic plasma concentration of the protein.

What is claimed is:

1. A method of inhibiting infection of a CD4+ cell by a human immunodeficiency virus which comprises contacting the human immunodeficiency virus with an amount of a CD4-IgG2 chimeric heterotetramer effective to form a complex with all such human immunodeficiency virus which is in the presence of the CD4+ cell so as to thereby inhibit infection of the CD4+ cell by the virus, wherein the CD4-IgG2 chimeric heterotetramer comprises two heavy chains and two light chains, the heavy chains being encoded by an expression vector designated CD4-IgG2HC-pRcCMV (ATCC No. 75193) and the light chains being encoded by an expression vector designated CD4-kLC-pRcCMV (ATCC No. 75194).

2. A method of preventing CD4+ cells of a subject from becoming infected with human immunodeficiency virus which comprises administering to the subject an amount of a CD4-IgG2 chimeric heterotetramer effective to bind to any human immunodeficiency virus present in the subject, so as to thereby prevent the subject's CD4+ cells from becoming infected with human immunodeficiency virus, wherein the CD4-IgG2 chimeric heterotetramer comprises two heavy chains and two light chains, the heavy chains being encoded by an expression vector designated CD4-IgG2HC-pRcCMV (ATCC No. 75193) and the light chains being encoded by an expression vector designated CD4-kLC-pRcCMV (ATCC No. 75194).

3. A method of treating a subject having CD4+ cells infected with human immunodeficiency virus which comprises administering to the subject an amount of a CD4-IgG2 chimeric heterotetramer effective to bind to any human immunodeficiency virus present in the subject, so as to thereby treat the subject having CD4+ cells infected with human immunodeficiency virus, wherein the CD4-IgG2 chimeric heterotetramer comprises two heavy chains and two light chains, the heavy chains being encoded by an expression vector designated CD4-IgG2HC-pRcCMV (ATCC No. 75193) and the light chains being encoded by an expression vector designated CD4-kLC-pRcCMV (ATCC No. 75194).

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 1796 base pairs
      (B) TYPE: nucleic acid
      (C) STRANDEDNESS: double
      (D) TOPOLOGY: unknown (ii) MOLECULE TYPE: cDNA (vi) ORIGINAL SOURCE:
      (A) ORGANISM: Homo sapiens
      (G) CELL TYPE: Lymphocyte (xi) SEQUENCE DESCRIPTION: SEQ ID NO:1:

```
CAAGCCCAGA GCCCTGCCAT TTCTGTGGGC TCAGGTCCCT ACTGCTCAGC CCCTTCCTCC      60

CTCGGCAAGG CCACAATGAA CCGGGGAGTC CCTTTTAGGC ACTTGCTTCT GGTGCTGCAA     120

CTGGCGCTCC TCCCAGCAGC CACTCAGGGA AAGAAAGTGG TGCTGGGCAA AAAAGGGGAT     180

ACAGTGGAAC TGACCTGTAC AGCTTCCCAG AAGAAGAGCA TACAATTCCA CTGGAAAAAC     240

TCCAACCAGA TAAAGATTCT GGGAAATCAG GGCTCCTTCT TAACTAAAGG TCCATCCAAG     300

CTGAATGATC GCGCTGACTC AAGAAGAAGC CTTTGGGACC AAGGAAACTT CCCCCTGATC     360

ATCAAGAATC TTAAGATAGA AGACTCAGAT ACTTACATCT GTGAAGTGGA GGACCAGAAG     420

GAGGAGGTGC AATTGCTAGT GTTCGGATTG ACTGCCAACT CTGACACCCA CCTGCTTCAG     480

GGGCAGAGCC TGACCCTGAC CTTGGAGAGC CCCCCTGGTA GTAGCCCCTC AGTGCAATGT     540

AGGAGTCCAA GGGGTAAAAA CATACAGGGG GGGAAGACCC TCTCCGTGTC TCAGCTGGAG     600

CTCCAGGATA GTGGCACCTG GACATGCACT GTCTTGCAGA ACCAGAAGAA GGTGGAGTTC     660

AAAATAGACA TCGTGGTGCT AGCTTTCGAG CGCAAATGTT GTGTCGAGTG CCCACCGTGC     720

CCAGGTAAGC CAGCCCAGGC CTCGCCCTCC AGCTCAAGGC GGGACAGGTG CCCTAGAGTA     780

GCCTGCATCC AGGGACAGGC CCCAGCTGGG TGCTGACACG TCCACCTCCA TCTCTTCCTC     840
```

```
AGCACCACCT GTGGCAGGAC CGTCAGTCTT CCTCTTCCCC CCAAAACCCA AGGACACCCT    900

CATGATCTCC CGGACCCCTG AGGTCACGTG CGTGGTGGTG GACGTGAGCC ACGAAGACCC    960

CGAGGTCCAG TTCAACTGGT ACGTGGACGG CGTGGAGGTG CATAATGCCA AGACAAAGCC   1020

ACGGGAGGAG CAGTTCAACA GCACGTTCCG TGTGGTCAGC GTCCTCACCG TTGTGCACCA   1080

GGACTGGCTG AACGGCAAGG AGTACAAGTG CAAGGTCTCC AACAAAGGCC TCCCAGCCCC   1140

CATCGAGAAA ACCATCTCCA AAACCAAAGG TGGGACCCGC GGGGTATGAG GGCCACATGG   1200

ACAGAGGCCG GCTCGGCCCA CCCTCTGCCC TGGGAGTGAC CGCTGTGCCA ACCTCTGTCC   1260

CTACAGGGCA GCCCCGAGAA CCACAGGTGT ACACCCTGCC CCCATCCCGG GAGGAGATGA   1320

CCAAGAACCA GGTCAGCCTG ACCTGCCTGG TCAAAGGCTT CTACCCCAGC GACATCGCCG   1380

TGGAGTGGGA GAGCAATGGG CAGCCGGAGA ACAACTACAA GACCACACCT CCCATGCTGG   1440

ACTCCGACGG CTCCTTCTTC CTCTACAGCA AGCTCACCGT GGACAAGAGC AGGTGGCAGC   1500

AGGGGAACTG CTTCTCATGC TCCGTGATGC ATGAGGCTCT GCACAACCAC TACACGCAGA   1560

AGAGCCTCTC CCTGTCTCCG GGTAAATGAG TGCCACGGCC GGCAAGCCCC CGCTCCCCAG   1620

GCTCTCGGGG TCGCGTGAGG ATGCTTGGCA CGTACCCCGT GTACATACTT CCCAGGCACC   1680

CAGCATGGAA ATAAAGCACC CAGCGCTGCC CTGGGCCCCT GCGAGACTGT GATGGTTCTT   1740

TCCGTGGGTC AGGCCGAGTC TGAGGCCTGA GTGGCATGAG GGAGGCAGAG TGGGTC       1796
```

(2) INFORMATION FOR SEQ ID NO:2:

(i) SEQUENCE CHARACTERISTICS:
        (A) LENGTH: 432 amino acids
        (B) TYPE: amino acid
        (C) STRANDEDNESS: unknown
        (D) TOPOLOGY: unknown (ii) MOLECULE TYPE: protein (vi) ORIGINAL SOURCE:
        (A) ORGANISM: homo sapien
        (G) CELL TYPE: lymphocyte (xi) SEQUENCE DESCRIPTION: SEQ ID NO:2:

```
Met Asn Arg Gly Val Pro Phe Arg His Leu Leu Val Leu Gln Leu
1               5                   10                  15

Ala Leu Leu Pro Ala Ala Thr Gln Gly Lys Lys Val Leu Gly Lys
                20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
        130                 135                 140

Ser Pro Pro Gly Ser Ser Pro Ser Val Gln Cys Arg Ser Pro Arg Gly
145                 150                 155                 160
```

```
Lys Asn Ile Gln Gly Gly Lys Thr Leu Ser Val Ser Gln Leu Glu Leu
                165                 170                 175
Gln Asp Ser Gly Thr Trp Thr Cys Thr Val Leu Gln Asn Gln Lys Lys
            180                 185                 190
Val Glu Phe Lys Ile Asp Ile Val Leu Ala Phe Glu Arg Lys Cys
        195                 200                 205
Cys Val Glu Cys Pro Pro Cys Pro Ala Pro Val Ala Gly Pro Ser
210                 215                 220
Val Phe Leu Phe Pro Pro Lys Pro Lys Asp Thr Leu Met Ile Ser Arg
225                 230                 235                 240
Thr Pro Glu Val Thr Cys Val Val Asp Val Ser His Glu Asp Pro
                245                 250                 255
Glu Val Gln Phe Asn Trp Tyr Val Asp Gly Val Glu Val His Asn Ala
                260                 265                 270
Lys Thr Lys Pro Arg Glu Glu Gln Phe Asn Ser Thr Phe Arg Val Val
            275                 280                 285
Ser Val Leu Thr Val Val His Gln Asp Trp Leu Asn Gly Lys Glu Tyr
            290                 295                 300
Lys Cys Lys Val Ser Asn Lys Gly Leu Pro Ala Pro Ile Glu Lys Thr
305                 310                 315                 320
Ile Ser Lys Thr Lys Gly Gln Pro Arg Glu Pro Gln Val Tyr Thr Leu
                325                 330                 335
Pro Pro Ser Arg Glu Glu Met Thr Lys Asn Gln Val Ser Leu Thr Cys
            340                 345                 350
Leu Val Lys Gly Phe Tyr Pro Ser Asp Ile Ala Val Glu Trp Glu Ser
            355                 360                 365
Asn Gly Gln Pro Glu Asn Asn Tyr Lys Thr Thr Pro Pro Met Leu Asp
            370                 375                 380
Ser Asp Gly Ser Phe Phe Leu Tyr Ser Lys Leu Thr Val Asp Lys Ser
385                 390                 395                 400
Arg Trp Gln Gln Gly Asn Val Phe Ser Cys Ser Val Met His Glu Ala
                405                 410                 415
Leu His Asn His Tyr Thr Gln Lys Ser Leu Ser Leu Ser Pro Gly Lys
                420                 425                 430

(2) INFORMATION FOR SEQ ID NO:3:

(i) SEQUENCE CHARACTERISTICS:
        (A) LENGTH: 2482 base pairs
        (B) TYPE: nucleic acid
        (C) STRANDEDNESS: double
        (D) TOPOLOGY: unknown (ii) MOLECULE TYPE: cDNA (vi) ORIGINAL SOURCE:
        (A) ORGANISM: homo sapien
        (G) CELL TYPE: lymphocyte (xi) SEQUENCE DESCRIPTION: SEQ ID NO:3:

CAAGCCCAGA GCCCTGCCAT TTCTGTGGGC TCAGGTCCCT ACTGCTCAGC CCCTTCCTCC      60

CTCGGCAAGG CCACAATGAA CCGGGGAGTC CCTTTTAGGC ACTTGCTTCT GGTGCTGCAA     120

CTGGCGCTCC TCCCAGCAGC CACTCAGGGA AAGAAAGTGG TGCTGGGCAA AAAAGGGGAT     180

ACAGTGGAAC TGACCTGTAC AGCTTCCCAG AAGAAGAGCA TACAATTCCA CTGGAAAAAC     240

TCCAACCAGA TAAAGATTCT GGGAAATCAG GGCTCCTTCT TAACTAAAGG TCCATCCAAG     300
```

```
CTGAATGATC GCGCTGACTC AAGAAGAAGC CTTTGGGACC AAGGAAACTT CCCCCTGATC      360

ATCAAGAATC TTAAGATAGA AGACTCAGAT ACTTACATCT GTGAAGTGGA GGACCAGAAG      420

GAGGAGGTGC AATTGCTAGT GTTCGGATTG ACTGCCAACT CTGACACCCA CCTGCTTCAG      480

GGGCAGAGCC TGACCCTGAC CTTGGAGAGC CCCCCTGGTA GTAGCCCCTC AGTGCAATGT      540

AGGAGTCCAA GGGGTAAAAA CATACAGGGG GGGAAGACCC TCTCCGTGTC TCAGCTGGAG      600

CTCCAGGATA GTGGCACCTG ACATGCACT GTCTTGCAGA ACCAGAAGAA GGTGGAGTTC       660

AAAATAGACA TCGTGGTGCT AGCTTTCGCC TCCACCAAGG GCCCATCGGT CTTCCCCCTG      720

GCGCCCTGCT CCAGGAGCAC CTCCGAGAGC ACAGCCGCCC TGGGCTGCCT GGTCAAGGAC      780

TACTTCCCCG AACCGGTGAC GGTGTCGTGG AACTCAGGCG CTCTGACCAG CGGCGTGCAC      840

ACCTTCCCAG CTGTCCTACA GTCCTCAGGA CTCTACTCCC TCAGCAGCGT GGTGACCGTG      900

CCCTCCAGCA ACTTCGGCAC CCAGACCTAC ACCTGCAACG TAGATCACAA GCCCAGCAAC      960

ACCAAGGTGG ACAAGACAGT TGGTGAGAGG CCAGCTCAGG GAGGGAGGGT GTCTGCTGGA     1020

AGCCAGGCTC AGCCCTCCTG CCTGGACGCA CCCCGGCTGT GCAGCCCCAG CCCAGGGCAG     1080

CAAGGCAGGC CCCATCTGTC TCCTCACCCG GAGGCCTCTG CCCGCCCCAC TCATGCTCAG     1140

GGAGAGGGTC TTCTGGCTTT TTCCACCAGG CTCCAGGCAG GCACAGGCTG GGTGCCCCTA     1200

CCCCAGGCCC TTCACACACA GGGGCAGGTG CTTGGCTCAG ACCTGCCAAA AGCCATATCC     1260

GGGAGGACCC TGCCCCTGAC CTAAGCCGAC CCCAAAGGCC AAACTGTCCA CTCCCTCAGC     1320

TCGGACACCT TCTCTCCTCC CAGATCCGAG TAACTCCCAA TCTTCTCTCT GCAGAGCGCA     1380

AATGTTGTGT CGAGTGCCCA CCGTGCCCAG GTAAGCCAGC CCAGGCCTCG CCCTCCAGCT     1440

CAAGGCGGGA CAGGTGCCCT AGAGTAGCCT GCATCCAGGG ACAGGCCCCA GCTGGGTGCT     1500

GACACGTCCA CCTCCATCTC TTCCTCAGCA CCACCTGTGG CAGGACCGTC AGTCTTCCTC     1560

TTCCCCCCAA AACCCAAGGA CACCCTCATG ATCTCCCGGA CCCCTGAGGT CACGTGCGTG     1620

GTGGTGGACG TGAGCCACGA AGACCCCGAG GTCCAGTTCA ACTGGTACGT GGACGGCGTG     1680

GAGGTGCATA ATGCCAAGAC AAAGCCACGG GAGGAGCAGT TCAACAGCAC GTTCCGTGTG     1740

GTCAGCGTCC TCACCGTTGT GCACCAGGAC TGGCTGAACG GCAAGGAGTA CAAGTGCAAG     1800

GTCTCCAACA AAGGCCTCCC AGCCCCCATC GAGAAAACCA TCTCCAAAAC CAAAGGTGGG     1860

ACCCGCGGGG TATGAGGGCC ACATGGACAG AGGCCGGCTC GGCCCACCCT CTGCCCTGGG     1920

AGTGACCGCT GTGCCAACCT CTGTCCCTAC AGGGCAGCCC CGAGAACCAC AGGTGTACAC     1980

CCTGCCCCCA TCCCGGGAGG AGATGACCAA GAACCAGGTC AGCCTGACCT GCCTGGTCAA     2040

AGGCTTCTAC CCCAGCGACA TCGCCGTGGA GTGGGAGAGC AATGGGCAGC CGGAGAACAA     2100

CTACAAGACC ACACCTCCCA TGCTGGACTC CGACGGCTCC TTCTTCCTCT ACAGCAAGCT     2160

CACCGTGGAC AAGAGCAGGT GGCAGCAGGG GAACGTCTTC TCATGCTCCG TGATGCATGA     2220

GGCTCTGCAC AACCACTACA CGCAGAAGAG CCTCTCCCTG TCTCCGGGTA AATGAGTGCC     2280

ACGGCCGGCA AGCCCCGCT CCCCAGGCTC TCGGGGTCGC GTGAGGATGC TTGGCACGTA      2340

CCCCGTGTAC ATACTTCCCA GGCACCCAGC ATGGAAATAA AGCACCCAGC GCTGCCCTGG     2400

GCCCCTGCGA GACTGTGATG GTTCTTTCCG TGGGTCAGGC CGAGTCTGAG GCCTGAGTGG     2460

CATGAGGGAG GCAGAGTGGG TC                                             2482
```

(2) INFORMATION FOR SEQ ID NO:4:

(i) SEQUENCE CHARACTERISTICS:
        (A) LENGTH: 530 amino acids

```
      (B) TYPE: amino acid
      (C) STRANDEDNESS: unknown
      (D) TOPOLOGY: unknown (ii) MOLECULE TYPE: cDNA (vi) ORIGINAL SOURCE:
       (A) ORGANISM: homo sapien
       (G) CELL TYPE: lymphocyte (xi) SEQUENCE DESCRIPTION: SEQ ID NO:4:

Met Asn Arg Gly Val Pro Phe Arg His Leu Leu Leu Val Leu Gln Leu
1               5                   10                  15

Ala Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
        50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Ala Ser Thr Lys
        195                 200                 205

Gly Pro Ser Val Phe Pro Leu Ala Pro Cys Ser Arg Ser Thr Ser Glu
    210                 215                 220

Ser Thr Ala Ala Leu Gly Cys Leu Val Lys Asp Tyr Phe Pro Glu Pro
225                 230                 235                 240

Val Thr Val Ser Trp Asn Ser Gly Ala Leu Thr Ser Gly Val His Thr
                245                 250                 255

Phe Pro Ala Val Leu Gln Ser Ser Gly Leu Tyr Ser Leu Ser Ser Val
            260                 265                 270

Val Thr Val Pro Ser Ser Asn Phe Gly Thr Gln Thr Tyr Thr Cys Asn
        275                 280                 285

Val Asp His Lys Pro Ser Asn Thr Lys Val Asp Lys Thr Val Glu Arg
    290                 295                 300

Lys Cys Cys Val Glu Cys Pro Pro Cys Pro Ala Pro Pro Val Ala Gly
305                 310                 315                 320

Pro Ser Val Phe Leu Phe Pro Pro Lys Pro Lys Asp Thr Leu Met Ile
                325                 330                 335

Ser Arg Thr Pro Glu Val Thr Cys Val Val Val Asp Val Ser His Glu
            340                 345                 350

Asp Pro Glu Val Gln Phe Asn Trp Tyr Val Asp Gly Val Glu Val His
```

```
                 355               360                 365
Asn Ala Lys Thr Lys Pro Arg Glu Glu Gln Phe Asn Ser Thr Phe Arg
    370                 375                 380

Val Val Ser Val Leu Thr Val Val His Gln Asp Trp Leu Asn Gly Lys
385                 390                 395                 400

Glu Tyr Lys Cys Lys Val Ser Asn Lys Gly Leu Pro Ala Pro Ile Glu
                405                 410                 415

Lys Thr Ile Ser Lys Thr Lys Gly Gln Pro Arg Glu Pro Gln Val Tyr
            420                 425                 430

Thr Leu Pro Pro Ser Arg Glu Glu Met Thr Lys Asn Gln Val Ser Leu
        435                 440                 445

Thr Cys Leu Val Lys Gly Phe Tyr Pro Ser Asp Ile Ala Val Glu Trp
    450                 455                 460

Glu Ser Asn Gly Gln Pro Glu Asn Asn Tyr Lys Thr Thr Pro Pro Met
465                 470                 475                 480

Leu Asp Ser Asp Gly Ser Phe Phe Leu Tyr Ser Lys Leu Thr Val Asp
                485                 490                 495

Lys Ser Arg Trp Gln Gln Gly Asn Val Phe Ser Cys Ser Val Met His
            500                 505                 510

Glu Ala Leu His Asn His Tyr Thr Gln Lys Ser Leu Ser Leu Ser Pro
        515                 520                 525

Gly Lys
530
```

(2) INFORMATION FOR SEQ ID NO:5:

(i) SEQUENCE CHARACTERISTICS:
        (A) LENGTH: 1149 base pairs
        (B) TYPE: nucleic acid
        (C) STRANDEDNESS: double
        (D) TOPOLOGY: unknown (ii) MOLECULE TYPE: cDNA (vi) ORIGINAL SOURCE:
        (A) ORGANISM: homo sapien
        (G) CELL TYPE: lymphocyte (xi) SEQUENCE DESCRIPTION: SEQ ID NO:5:

```
CAAGCCCAGA GCCCTGCCAT TTCTGTGGGC TCAGGTCCCT ACTGCTCAGC CCCTTCCTCC      60
CTCGGCAAGG CCACAATGAA CCGGGGAGTC CCTTTTAGGC ACTTGCTTCT GGTGCTGCAA     120
CTGGCGCTCC TCCCAGCAGC CACTCAGGGA AAGAAAGTGG TGCTGGGCAA AAAAGGGGAT     180
ACAGTGGAAC TGACCTGTAC AGCTTCCCAG AAGAAGAGCA TACAATTCCA CTGGAAAAAC     240
TCCAACCAGA TAAAGATTCT GGGAAATCAG GGCTCCTTCT TAACTAAAGG TCCATCCAAG     300
CTGAATGATC GCGCTGACTC AAGAAGAAGC CTTTGGGACC AAGGAAACTT CCCCCTGATC     360
ATCAAGAATC TTAAGATAGA AGACTCAGAT ACTTACATCT GTGAAGTGGA GGACCAGAAG     420
GAGGAGGTGC AATTGCTAGT GTTCGGATTG ACTGCCAACT CTGACACCCA CCTGCTTCAG     480
GGGCAGAGCC TGACCCTGAC CTTGGAGAGC CCCCCTGGTA GTAGCCCCTC AGTGCAATGT     540
AGGAGTCCAA GGGGTAAAAA CATACAGGGG GGAAGACCC TCTCCGTGTC TCAGCTGGAG      600
CTCCAGGATA GTGGCACCTG GACATGCACT GTCTTGCAGA ACCAGAAGAA GGTGGAGTTC     660
AAAATAGACA TCGTGGTGCT AGCTTTCACT GTGGCTGCAC CATCTGTCTT CATCTTCCCG     720
CCATCTGATG AGCAGTTGAA ATCTGGAACT GCCTCTGTTG TGTGCCTGCT GAATAACTTC     780
TATCCCAGAG AGGCCAAAGT ACAGTGGAAG GTGGATAACG CCCTCCAATC GGGTAACTCC     840
```

```
CAGGAGAGTG TCACAGAGCA GGACAGCAAG GACAGCACCT ACAGCCTCAG CAGCACCCTG      900

ACGCTGAGCA AAGCAGACTA CGAGAAACAC AAAGTCTACG CCTGCGAAGT CACCCATCAG      960

GGCCTGAGCT CGCCCGTCAC AAAGAGCTTC AACAGGGGAG AGTGTTAGAG GGAGAAGTGC     1020

CCCCACCTGC TCCTCAGTTC CAGCCTGACC CCCTCCCATC CTTTGGCCTC TGACCCTTTT     1080

TCCACAGGGG ACCTACCCCT ATTGCGGTCC TCCAAGCTCA TCTTTCACCT CACCCCCCTC     1140

CTCCTCCTT                                                             1149
```

(2) INFORMATION FOR SEQ ID NO:6:

(i) SEQUENCE CHARACTERISTICS:
        (A) LENGTH: 310 amino acids
        (B) TYPE: amino acid
        (C) STRANDEDNESS: unknown
        (D) TOPOLOGY: unknown (ii) MOLECULE TYPE: protein (vi) ORIGINAL SOURCE:
        (A) ORGANISM: homo sapien
        (G) CELL TYPE: lymphocyte (xi) SEQUENCE DESCRIPTION: SEQ ID NO:6:

```
Met Asn Arg Gly Val Pro Phe Arg His Leu Leu Leu Val Leu Gln Leu
1               5                  10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Thr Val Ala Ala
        195                 200                 205

Pro Ser Val Phe Ile Phe Pro Pro Ser Asp Glu Gln Leu Lys Ser Gly
    210                 215                 220

Thr Ala Ser Val Val Cys Leu Leu Asn Asn Phe Tyr Pro Arg Glu Ala
225                 230                 235                 240

Lys Val Gln Trp Lys Val Asp Asn Ala Leu Gln Ser Gly Asn Ser Gln
                245                 250                 255

Glu Ser Val Thr Glu Gln Asp Ser Lys Asp Ser Thr Tyr Ser Leu Ser
```

```
                    260             265             270
Ser Thr Leu Thr Leu Ser Lys Ala Asp Tyr Glu Lys His Lys Val Tyr
            275             280             285
Ala Cys Glu Val Thr His Gln Gly Leu Ser Ser Pro Val Thr Lys Ser
    290             295             300
Phe Asn Arg Gly Glu Cys
305             310
```

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: unknown (ii) MOLECULE TYPE: synthetic DNA (vi) ORIGINAL SOURCE:
        (A) ORGANISM:
        (G) CELL TYPE:

(xi) SEQUENCE DESCRIPTION: SEQ ID NO:7:

GACACAACAT TTGCGCTCGA AAGCTAGCAC CACG                          34

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: unknown (ii) MOLECULE TYPE: synthetic DNA (vi) ORIGINAL SOURCE:
        (A) ORGANISM:
        (G) CELL TYPE:

(xi) SEQUENCE DESCRIPTION: SEQ ID NO:8:

GGGCCCTTGG TGGAGGCGAA AGCTAGCACC ACG                           33

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: unknown (ii) MOLECULE TYPE: synthetic DNA (vi) ORIGINAL SOURCE:
        (A) ORGANISM:
        (G) CELL TYPE:

(xi) SEQUENCE DESCRIPTION: SEQ ID NO:9:

GATGGTGCAG CCACAGTGAA AGCTAGCACC ACG                           33